(12) United States Patent
Park

(10) Patent No.: US 7,727,259 B2
(45) Date of Patent: Jun. 1, 2010

(54) BIO-FLEXIBLE SPINAL FIXATION APPARATUS WITH SHAPE MEMORY ALLOY

(76) Inventor: Kyung-Woo Park, 995-25, Daechi 3-Dong, Kangnam-Gu, Seoul 135-283 (KR)

( * ) Notice: Subject to any disclaimer, the term of this patent is extended or adjusted under 35 U.S.C. 154(b) by 1442 days.

(21) Appl. No.: 11/044,268

(22) Filed: Jan. 28, 2005

(65) Prior Publication Data

US 2006/0064090 A1 Mar. 23, 2006

(30) Foreign Application Priority Data

Sep. 22, 2004 (KR) .................. 10-2004-0076105
Sep. 22, 2004 (KR) .................. 10-2004-0076106
Nov. 26, 2004 (KR) .................. 10-2004-0097833
Nov. 26, 2004 (KR) .................. 10-2004-0097834

(51) Int. Cl.
*A61B 17/70* (2006.01)

(52) U.S. Cl. ..................................... 606/255

(58) Field of Classification Search ............... 606/61, 606/78, 254, 255, 257, 264, 265, 267, 271, 606/272; 623/17.13; 403/197, 206, 208, 403/212, 213, 231, 240, 241, 244, 245, 246
See application file for complete search history.

(56) References Cited

U.S. PATENT DOCUMENTS

| 4,805,602 | A | * | 2/1989 | Puno et al. ................ 606/61 |
| 5,498,262 | A | | 3/1996 | Bryan |
| 5,672,175 | A | * | 9/1997 | Martin .................... 606/86 A |
| 6,197,028 | B1 | | 3/2001 | Ray et al. |
| 6,280,443 | B1 | | 8/2001 | Gu et al. |
| 6,293,949 | B1 | | 9/2001 | Justis et al. |
| 6,520,990 | B1 | | 2/2003 | Ray |
| 6,565,566 | B1 | | 5/2003 | Wagner et al. |
| 6,669,697 | B1 | | 12/2003 | Pisharodi |
| 6,783,526 | B1 | | 8/2004 | Lin et al. |
| 6,802,844 | B2 | * | 10/2004 | Ferree ..................... 606/258 |
| 2001/0023350 | A1 | * | 9/2001 | Choi ....................... 606/61 |
| 2003/0153914 | A1 | | 8/2003 | Oribe et al. |
| 2003/0220643 | A1 | * | 11/2003 | Ferree ..................... 606/61 |
| 2004/0049188 | A1 | | 3/2004 | Slivka |

FOREIGN PATENT DOCUMENTS

FR 2 846 223 4/2004

(Continued)

OTHER PUBLICATIONS

Supplementary European Search Report dated Nov. 19, 2008 for European Application No. EP 04 80 8432.

*Primary Examiner*—Eduardo C Robert
*Assistant Examiner*—Elana B Fisher
(74) *Attorney, Agent, or Firm*—Collard & Roe, PC

(57) ABSTRACT

The present invention relates to a spinal fixation apparatus having a segment flexible rod for connecting pedicle screws and a transverse link for spacing out the rods, which are made from a shape memory alloy, thereby easily and simply connecting the rods and the pedicle screws. According to the present invention, it can easily and simply fit the rods to the misaligned pedicle screw, even if it may be a failure of alignment of the pedicle screws in surgery. Also, it can easily set up the transverse link on a pair of the longitudinal rods, even if the longitudinal rods are declined or are not in parallel.

4 Claims, 20 Drawing Sheets

FOREIGN PATENT DOCUMENTS

| | | |
|---|---|---|
| JP | 04-244149 | 1/1992 |
| JP | 07-255759 | 9/1995 |
| JP | 2003529415 | 10/2003 |
| KR | 2000-0011302 | 6/2000 |
| KR | 20-0250854 | 10/2001 |
| KR | 20-0338006 | 12/2003 |
| WO | WO 02/085217 | 10/2002 |
| WO | WO 02/102259 | 12/2002 |
| WO | WO02/102259 | * 12/2002 |
| WO | WO 03/039330 | 5/2003 |
| WO | WO 03/094692 | 11/2003 |

* cited by examiner

BIO-FLEXIBLE SPINAL FIXATION APPARATUS WITH SHAPE MEMORY ALLOY

BACKGROUND OF THE INVENTION

1. Field of the Invention

The present invention relates to a spinal fixation apparatus which can correct and immobilize injured or deformed human spine; and, more particularly, to a spine fixation apparatus for easily carrying out an operation on the spine, by using segment flexible rods and a transverse link which are made from a shape memory alloy, so that the rod and the transverse link can elongate in different shapes with flexibility.

2. Description of the Related Art

Typically, the vertebra typically consists of 24 bones (except for sacral vertebra). They are connected to each other through joint segments and there are discs between the joint segments. By this structure, the vertebra has man's posture kept and a shock absorbed. Also, the vertebra is essential to exercises and protects all internal organs from an external shock. However, the vertebra of the spine can be injured or wrenched by external environments, abnormal postures for a long time and anaplastia and so on, which may induce a serious back pain by pressing the nerve system passing through the spine.

Patients, who have been injured in a part of his spine, cannot take their activities in daily life, because the injured part of the spine is compressed by adjacent other parts of the spine. This spinal disorder requires a surgical intervention to treat the pain which is induced in nerve root by the compression and unstableness of intervertebral joints.

As shown in FIG. 1, a conventional spinal fixation apparatus includes a plurality of pedicle screws 200 which are respectively inserted through the pedicle into injured or deformed vertebra, wherein each of the pedicle screws 200 has a head 201 formed at a top portion thereof, wherein the head 201 has a U-shaped rod passage 201a and a female thread 201b is formed on an inner surface thereof, and wherein a thread 202 is formed below the head 201 in order that the pedicle screws 200 can be implanted into the vertebra; a pair of longitudinal rods 250 which are located in both laterals of the spine and coupled to the pedicle screws 200 for preventing a movement of the vertebra; a number of set screws 300, each of which has a male thread and a wrench hole 300a on an upper surface thereof, being inserted into the rod passage 201a of the head 201 of the pedicle screw 200 for preventing a movement of the rod; and a transverse link 400 for holding the longitudinal rods 250.

In the conventional spinal fixation apparatus, the rods and the pedicle screws will be described in short, referring to the accompanying drawing.

As shown in FIG. 2, the thread 202 of the pedicle screws 200 is implanted into the vertebral body 500. The rod 250 is then put into the rod passage 201a. In this situation, the set screw 300 is joined to the female thread 201b of the rod passage 201a.

Also, the set screw 300 is joined to the rod passage 201a, by inserting it into a groove 300a and turning it with a wrench on the top thereof. As a result, the bottom side of the set screw 300 compresses the top of the rod 250 within the rod passage 201a of the pedicle screws 200.

According to this assembly, the rod 250 is definitely tightened up on the pedicle screw 200 to correct the diseased or injured vertebral body 500. The both ends of the transverse link 400 are coupled to the pair of the rods 250 so that the transverse link 400 is laid across the rods 250 which is connected to the pedicle screws 200. When a patient gets to do a wrenched action toward his left or right sides, the transverse link 400 prevents a rotation and migration of the rod 250.

In the conventional spinal fixation apparatus, the rod 250 functions as a basic element to correct the vertebra. Therefore, the material of the rods or the properties of the rod, such as elasticity, has a large effect on human body, after it is inseparably fused together with the vertebra. The rod 250 itself is not elastic because it is made from a titan alloy for medicine. It is very difficult to keep the line of his lumber normal since the vertebra segment is fused together with the rod to correct the vertebra bodies.

Also, after the vertebra is integrally fused together with the rod, the weight is concentrated upon the upper segment or the lower segment so that it will cause another vertebra stegnotic or instability of a lumbar vertebra within a few years after the vertebra fusion.

In particular, it has some problems in that the rod can be broken and buried in the vertebra, when a shock is inflicted upon the lumbar vertebra.

The rod is made to have a normal spinal curvature shape without being related to a specific spinal shape of individual. That causes the difficulty of standardizing each single products and making various shapes, thereby increasing the cost of products. Also, the rod structure induces a series of bottlenecks in connecting the pedicle screw to the rod because the rod has a straight shape. That is, the individual spinal shape is different from each other. Therefore, if the pedicle screws are not fixed uniformly between the segments, it was very difficult to install the straight rod on the pedicle screws. This is caused by the physical properties of the rod. In this case, an operator has to adjust a distance and direction of the pedicle screw based on the location of the rod, by making the pedicle screw slanted. Also, the operator has to adjust an angle of the pedicle screw's head, using the polyaxial type screw, which can freely rotate a head around the screw in a range of predetermined angle and set the rod up thereon. The operating work using the conventional vertebra fixation apparatus needs accuracy, because he must correctly grasp the location to install the pedicle screw and then have to make a hole in vertebra with a burden on the surgeon. Also, it takes a lot of times to make the rod based on a curved shape of patient's vertebra and to set the location of pedicle screw.

To solve the problems of the conventional vertebra fixation apparatus, the various types of the rods has been provided with elasticity, An example of an elastic rod for connecting the pedicle screws is illustrated in Korean utility model No. 0,338,006. This rod comprises a rod body 601 and an elastic connection portion 603 formed in the middle of the rod body 601. As shown in FIG. 3, the elastic rod is in various types, such as a semicircular ring, a coil spring, a bar type smaller then the diameter of the rod body, and the like.

These types provide the elastic connection portion for the rod in order that the rod body can be bent. This structure is capable of giving fluidity to the rod in a predetermined range between the pedicle segments. However, the rod structure results in a lose of the basic function of the spine correction since the elastic connection portion causes large movement. That is, the rod has to support and connect the spinal segments. In the above-mentioned structure, the pieces of the rod body are detachable so that they are freely movable in a given elastic range. Therefore, the secure connection between the spinal segments is not achieved.

Also, when the pedicle screws are out of the straight line, the rod structure has a problem in that it is difficult to connect the rod to the pedicle screw.

FIG. 4 shows a perspective view of the conventional transverse link 400 for preventing the pedicle from a minute movement.

The transverse link 400 comprises a fixed type housing 410 and a movable type housing 420 which are respectively hooked on both ends of the rod 250; a space bar 430 supported on the rod 250; and a set screw 440 connected with the fixed type housing 410 and the movable type housing 420 so that the space bar 430 is fixed to the rod 250.

The fixed type housing 410 and the movable type housing 420 respectively include half circle hooks 410a and 420a for connection on the rod 250; support holes 410b and 420b inserted into the both ends of the rod 250; screw holes 410c and 420c into which set screws 440 are inserted.

The hook 410a of the fixed type housing 410 is hooked on the rod 250 and then one end of the space bar 430 is inserted into the support hole 410b. The hook 420a of the movable type housing 420 is hooked on the rod 250 and then another end of the space bar 430 is inserted into the support hole 420b. The set screws 440 are joined to the screw holes 410c and 420c respectively, for securely tightening the rod 250 under the space bar 430.

In the structure of the transverse link 400, the inner diameter of the hook 410a is almost equal to that of the rod 250. Therefore, if one of the rods 250 is tilted or they are not in parallel, the transverse link 400 cannot comply with such a declination or unbalance of the rods 250. In case of the declination or unbalance of the rods 250, the support holes 410a and 420a of the fixed type housing 410 and movable type housing 420 are also unbalanced and thus the space bar 430 cannot be inserted into the support holes 410b and 420b. If strength is put on the space bar 430 for fixation on the support holes 410b and 420b, the position of the movable type housing 420 may be wrenched and distorted so that the rod 250 may be separated from the hook 420a of the movable type housing 420. In this case, even if the set screw 440 is joined to the screw hole 430, it is impossible to securely support the space bar 430 upon the rod 250. This problem in the transverse link 400 requires to take a long time for an operation on the surgery. In case where it is difficult to assemble the transverse link 400, it may be omitted; however, this will cause a defect of the surgery.

SUMMARY OF THE INVENTION

To solve the problems, a primary object of the present invention is to provide a spinal fixation apparatus which can easily and simply achieve a connection between a pedicle screw and a rod, even if it is slightly out of alignment of the pedicle screws during surgery, by deforming the shape and length of each of the rods and the transverse link which are made from a shape memory alloy of which the shape is changed at a specific temperature.

Another object of the present invention is to provide a spinal fixation apparatus which has a strength enough to correct the spine during the restoration from an elastic force so that the spinal fixation apparatus gives flexible behavior to corrected vertebral segments.

Further, another object of the present invention is to provide a staple type rod which is made from a shape memory alloy. The staple type rod of the present invention can easily and simply perform an operation of the vertebra correction and reduce the number of parts, being implanted directly into selected vertebra without a pedicle screw.

In accordance with one aspect of the present invention, there are provided a spinal fixation apparatus comprising: a plurality of pedicle screws, each of which has a head formed at a top portion thereof and a thread formed below the head to be implanted into a pedicle of a vertebra, wherein the head has a reception cavity and at least one rod groove on a bottom surface of the reception cavity; a pair of rods connected to the pedicle screws for preventing a movement of the vertebra, wherein the rods has an elasticity section therein and are mounted on the rod groove in the reception cavity; at least one transverse link which has an elasticity section in a straight member and hooks extended from both ends of the straight member for rigidly holding the pair of rods; and a plurality of set screws, each of which is rigidly inserted into the reception cavity of the head, preventing a movement of the rod, wherein the rods and the transverse link are made from a shape memory alloy which can be deformed at a predetermined temperature.

In accordance with another aspect of the present invention, there are provided a spinal fixation apparatus comprising: a plurality of pedicle screws, each of which has a head formed at a top portion thereof and a thread formed below the head to be implanted into a pedicle of a vertebra, wherein the head has a first rod groove formed in a bottom surface of the head; a plurality of head caps for covering the head of the pedicle screw, wherein the head cap has a second rod groove formed on an inner surface thereof; a pair of rods surrounded by the first rod groove of the head and the second rod groove of the head cap, preventing a movement of the vertebra, wherein the rods has an elasticity section therein; at least one transverse link which has an elasticity section in a straight member and hooks extended from both ends of the straight member for rigidly holding the pair of rods; and a plurality of fixing means, each of which tightens the head cap to the head of the pedicle screw, being inserted into the reception cavity of the head of the pedicle screws for preventing a movement of the rod, wherein the rods and the transverse link are made from a shape memory alloy which can be deformed at a predetermined temperature.

In accordance with further another aspect of the present invention, there are provided a spinal fixation apparatus comprising: a plurality of pedicle screws, each of which has a head formed at a top portion thereof and a thread formed below the head to be implanted into a pedicle of a vertebra, wherein the head has a reception cavity and two parallel rod grooves in a bottom surface of the reception cavity; a pair of rods connected to the pedicle screws for preventing a movement of the vertebra, wherein the rod is made of shape memory alloy which can be transformed in designated temperature and wherein the rods includes: 1) a straight bar placed in line with a center of the heads; 2) an elastic section formed in the straight bar; and 3) support bars having bending portions extended from both ends of the straight bar and bent along an outer surface of the head and line portions extended from both ends of the bending portions and put in the rod grooves, and a plurality of set members, each of which is inserted into the reception cavity of the head of the pedicle screws for preventing a movement of the rods.

In accordance with still another aspect of the present invention, there are provided a spinal fixation apparatus comprising: a plurality of pedicle screws, each of which has a head formed at a top portion thereof, and a thread formed below the head to be implanted into a pedicle of a vertebra, wherein the head has at least one circular groove on an outer surface thereof; and a pair of rods connected to the pedicle screws for preventing a movement of the vertebra, wherein each of the rods has a straight bar placed in line with a center line of the heads, an elastic section formed in the straight bar, support rings wound on the circular grooves of the heads, wherein the rods are made from a shape memory alloy which can be deformed at a predetermined temperature.

In accordance with still another aspect of the present invention, there are provided a spinal fixation apparatus comprising: a plurality of pedicle screws, each of which has a head formed at a top portion thereof, and a thread formed below the head to be implanted into a pedicle of a vertebra, wherein the head has a horizontal opening passing through a head body and a perpendicular thread hole to receive a fixing means; a pair of rods connected to the pedicle screws for preventing a movement of the vertebra, wherein the rods has a straight bar, and hooks extended from both ends of the straight bar and bent to be inserted into the horizontal opening, wherein the rods are made from a shape memory alloy which can be deformed at a predetermined temperature; and a plurality of fixing means for preventing a movement of the rod through the perpendicular thread hole of the head.

In accordance with still another aspect of the present invention, there are provided a spinal fixation apparatus comprising: a plurality of pedicle screws, each of which has a head formed at a top portion thereof and a thread formed below the head to be implanted into a pedicle of a vertebra, wherein the head has a reception cavity and two parallel rod grooves in a bottom surface of the reception cavity; a pair of rods connected to the pedicle screws for preventing a movement of the vertebra, wherein each of the rods has a "U" shape and wherein the rods are made from a shape memory alloy which can be deformed at a predetermined temperature; and a plurality of set members, each of which is inserted into the reception cavity of the head of the pedicle screws for preventing a movement of the rod.

In accordance with still another aspect of the present invention, there are provided a spinal fixation apparatus comprising: at least one pedicle screw which has a head at a top portion thereof and a thread formed below the head to be implanted into a pedicle of a vertebra, wherein the head has a reception cavity and two parallel sockets formed in a bottom of the reception cavity; a pair of staple rods connected to the pedicle screws for preventing a movement of the vertebra, wherein one side of each of the rods is directly implanted into a pedicle of the vertebra and the other side is inserted into one of the sockets; and at least one set member which is inserted into the reception cavity of the head of the pedicle screws for preventing a movement of the rod.

In accordance with still another aspect of the present invention, there are provided a spinal fixation apparatus comprising: at least one staple rods each of which has a bridge member for providing a space between a selected vertebra and an adjacent vertebra, an elastic section formed in the bridge member and a spike member to be implanted into the pedicle of a vertebra, wherein the spike member is downwardly extended from both ends of the bridge member, wherein the rod is made of shape memory alloy which can be deformed at a predetermined temperature.

In accordance with still another aspect of the present invention, there are provided a spinal fixation apparatus comprising: a plurality of pedicle screws having a head part; and a pair of rods for connecting the pedicle screws, wherein the rods are in a first structure at a first temperature range and are in a second structure at a second temperature range, wherein the second structure is a memorized shape of a shape memory alloy, and wherein the rods provide a handling margin in the first structure so that the rods of the memorized shape are more tight than those of the first structure, wherein the head part has a fixating means for securely fixing the rod and end parts of the rod are joined to the fixating means.

In accordance with still another aspect of the present invention, a spinal fixation apparatus comprising: first and second pedicle screw arrays perpendicularly arranged, substantially being in parallel to each other, wherein each of the first and second pedicle screw arrays includes: a) a plurality of pedicle screws joined to vertebras of human spine, each pedicle screw includes: 1) a head having a plurality of reception means; and 2) a male thread formed on a leg part to be implanted into the vertebras; and b) first and second rod arrays respectively connected the first and second pedicle screw arrays, wherein each of the first and second rod arrays includes a plurality of segment rods and wherein an end of each the segment rod is safely secured to one of the plurality of reception means, wherein the segment rods are a shape memory alloy.

BRIEF DESCRIPTION OF THE DRAWINGS

Other objects and benefits of the present invention will become apparent upon consideration of the following written description taken in conjunction with the following figures.

DETAILED DESCRIPTION OF THE PREFERRED EMBODIMENTS

Hereinafter, the present invention will be described in detail referring to the accompanying drawings. A spinal fixation apparatus according to the present invention can easily correct injured spines by using rods and transverse links which are made from a shape memory alloy. In particular, the rods and transverse links are made out of Nitinol alloy (Ni—Ti alloy) which has a superelastic characteristic.

A first embodiment will be described in detail referring to FIGS. 5 to 14.

According to the first embodiment of present invention, the spinal fixation apparatus includes a plurality of pedicle screws 1 implanted into the patient's vertebra; a pair of rods 2 located in both laterals of the spine and connected to the pedicle screws for preventing a movement of the vertebra; and a number of transverse links 3 for providing space between the rods.

Figure 1:
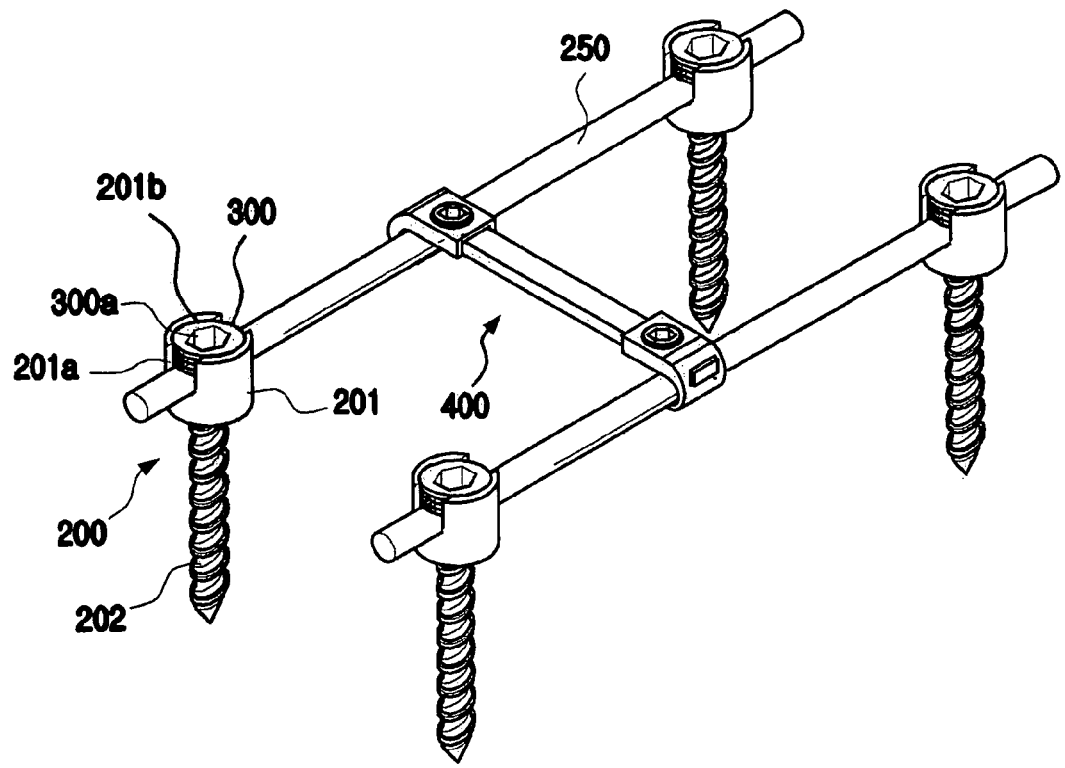
FIG. 1 is a perspective view illustrating a conventional spine fixation apparatus.
Figure 2:
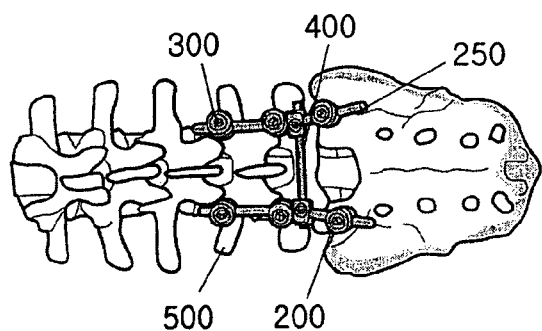
FIG. 2 is a perspective view illustrating a conventional spine fixation apparatus applied to the lumbar spine.
Figure 3:
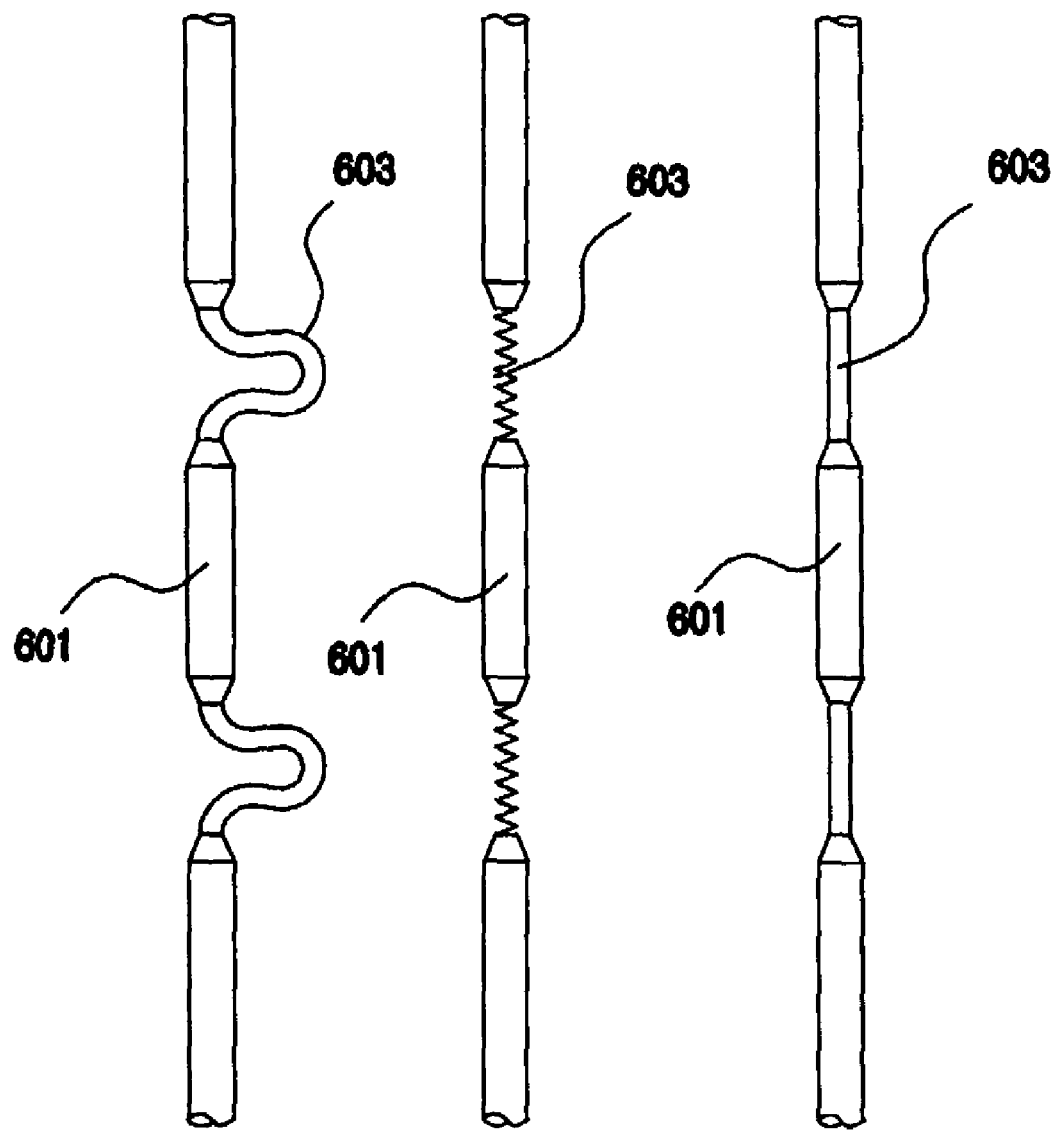
FIG. 3 is a plan view illustrating various forms of conventional rods.
Figure 4:
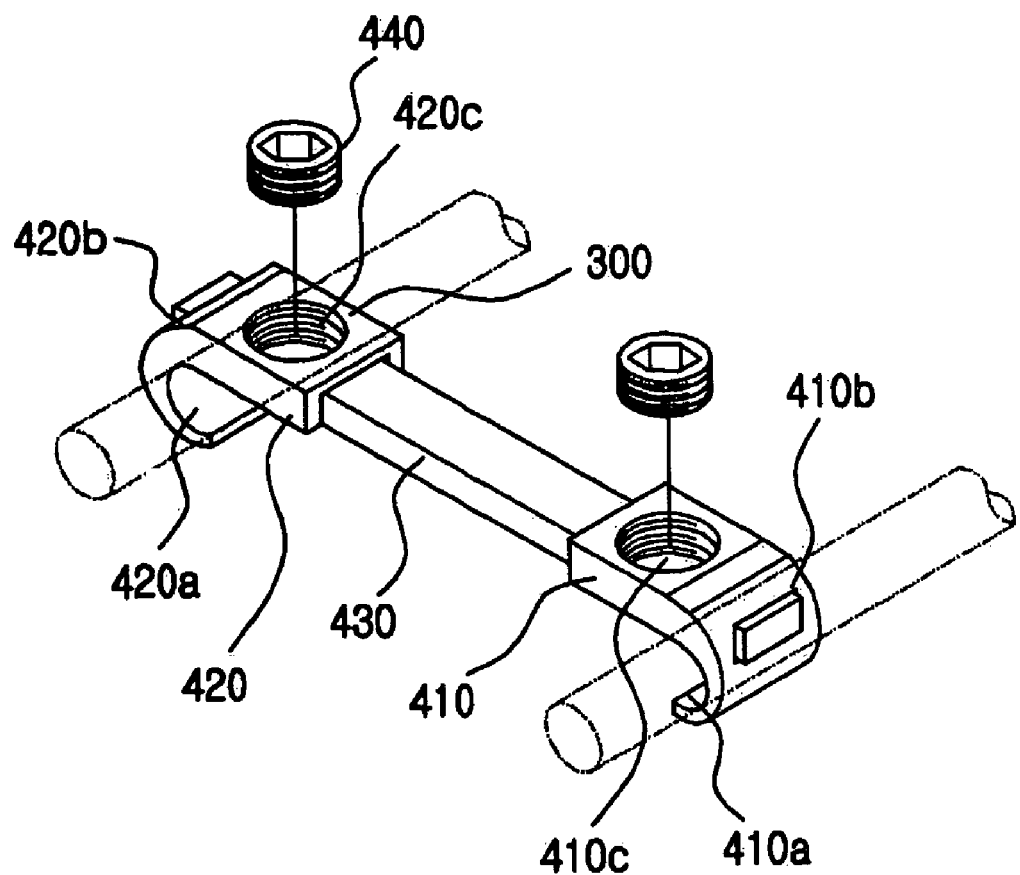
FIG. 4 is a perspective view illustrating a conventional transverse link applied to the rods.
Figure 5:
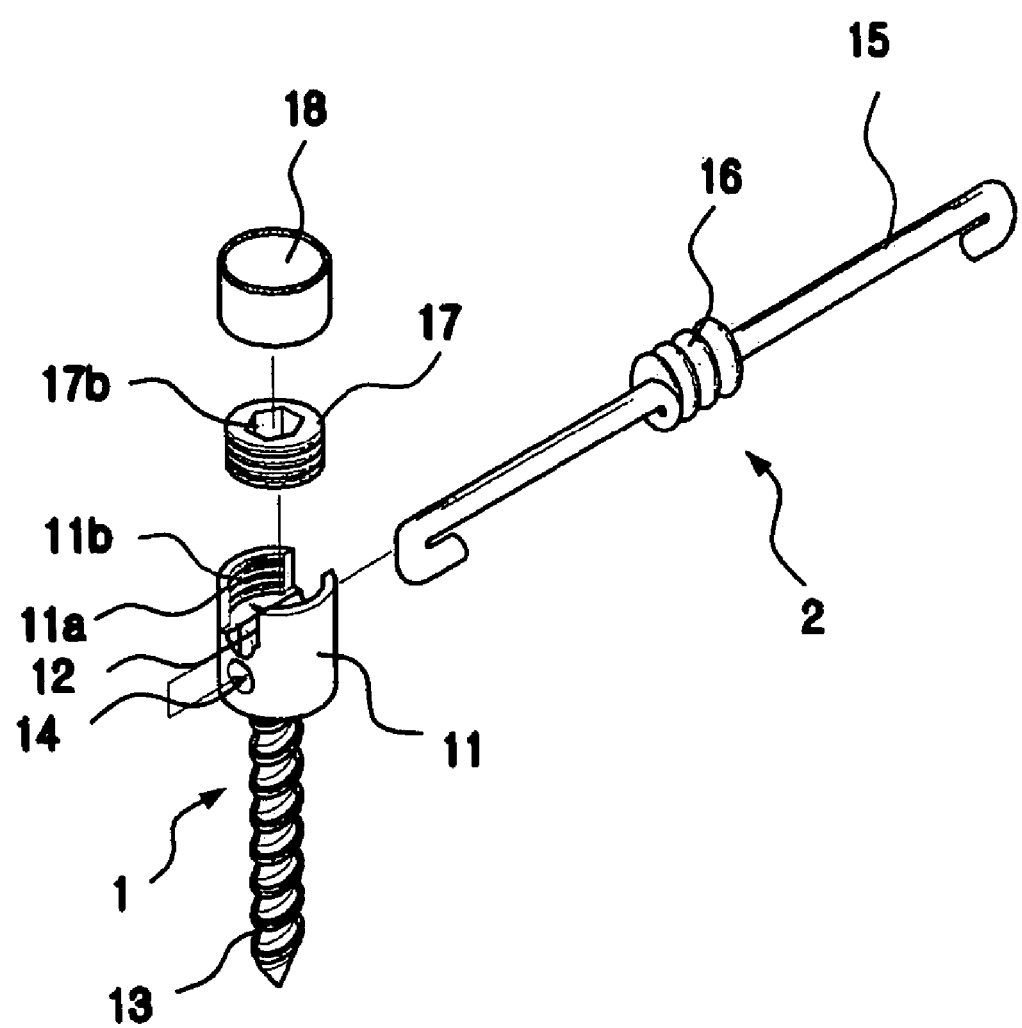
FIG. 5 is a perspective view illustrating a spine fixation apparatus according to a first embodiment of the present invention.
Figure 6:
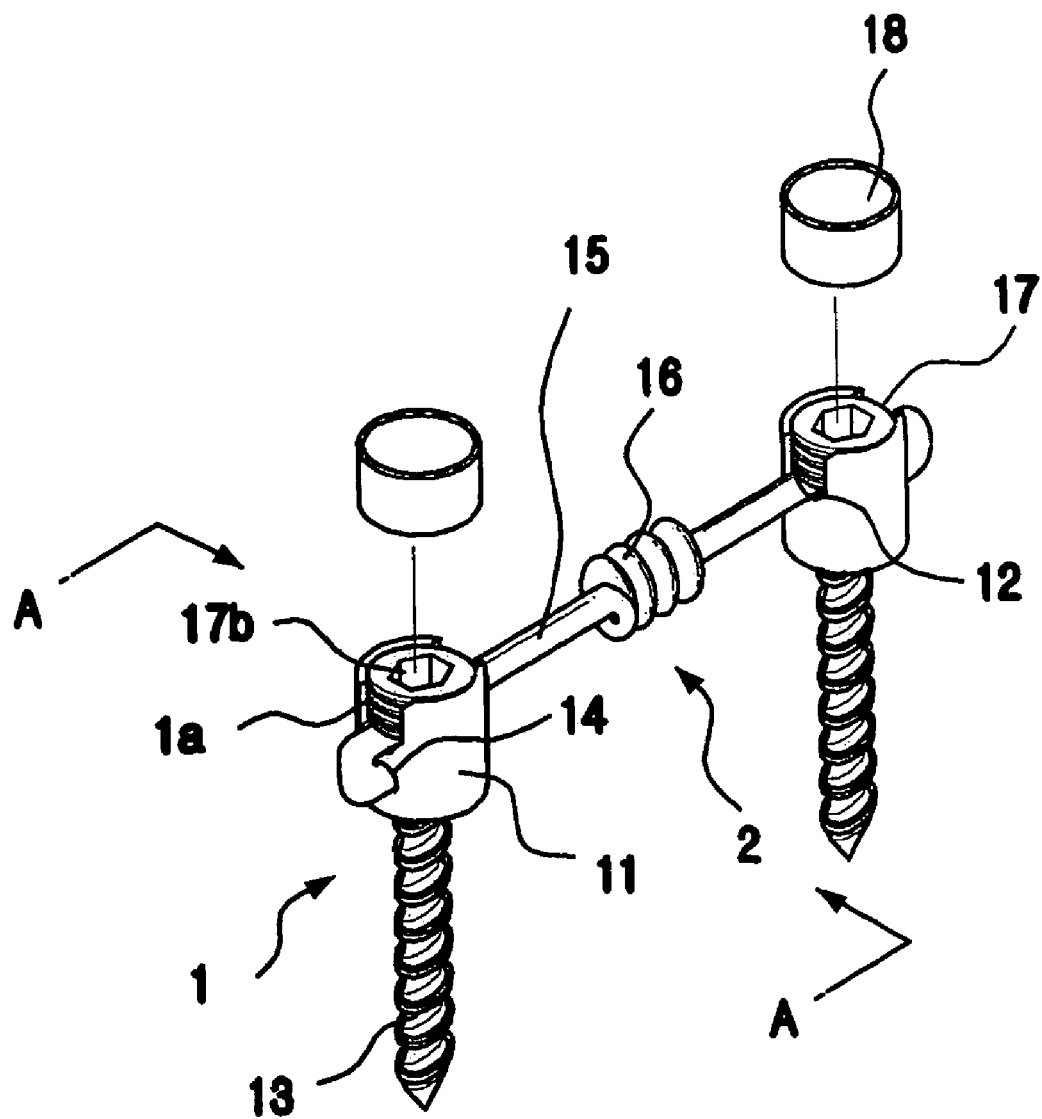
FIG. 6 is a perspective view illustrating an assembly of the spine fixation apparatus shown in FIG. 5.
Figure 7:
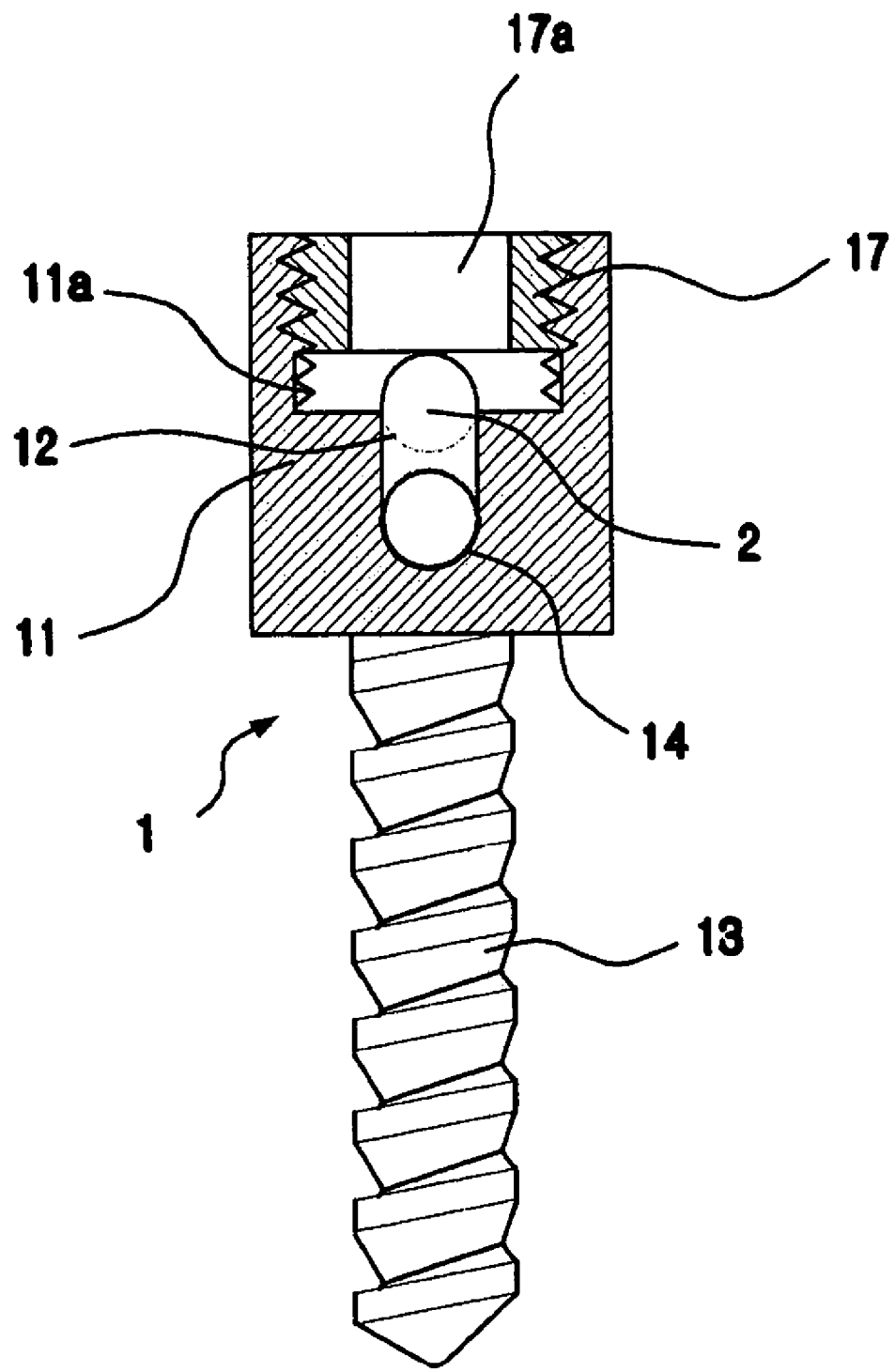
FIG. 7 is a cross-section view taken along A-A line shown in FIG. 6.

Referring now to FIGS. 5 to 7, the pedicle screw 1 comprises a head 11 formed at a top portion thereof and a thread 13 formed below the head to be implanted into the vertebra. The head 1 has a reception cavity 11a to receive the rod 2 and at least one rod groove 12 at the bottom of the reception cavity 11a. A diameter of the rod groove 12 corresponds to that of the rod 2.

The rod 2 has a rod body 15 which is bent and then has a hook shape at both ends thereof and the rod 2 has an elasticity section 16 formed in the middle of the rod body 15 to generate an elastic force corresponding to a shock which is inflicted on the patient's vertebra.

Figure 8:
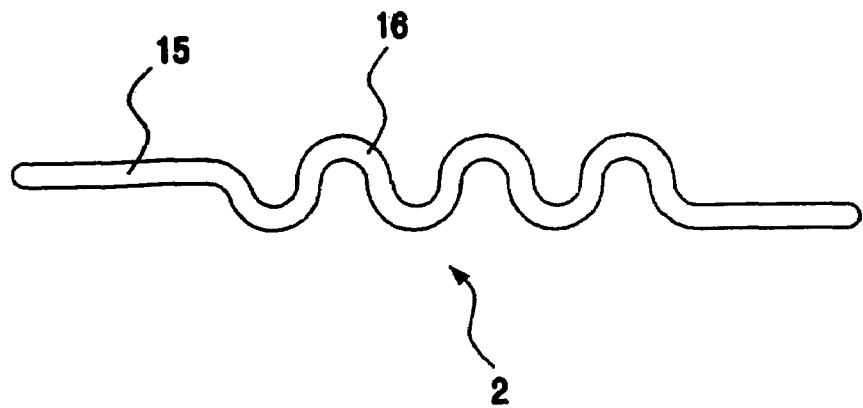
FIG. 8 is a plan view illustrating another form of the rod in the first embodiment of the present invention.

The elasticity section 16 is made of a coil spring. The coil spring is equal to the rod body 15 in their diameters. Another form of the elasticity section 16 is shown in a wave shape as shown in FIG. 8. The diameter of the rod is approximately in a range of 2 to 7 mm and it can be adjusted on a basis of unit diameter of 0.5 mm.

The elasticity section 16 serves as a buffer between spinal segments when the pedicle screw 1 is fused together with the spine. That is, when patients bends or wrenches his waist or an shock is inflicted on his waist, the elasticity section 16 can alleviate stimuli which are caused by patients' activities or the external shock.

A set screw 17 is inserted into the reception cavity 11a of the head 11 of the pedicle screws 1 for preventing a movement of the rod 2. The set screw 17 has an outer thread 17a for securely tightening the rod 2 and a recess 17b having a hexagonal cross-section view on the upper portion thereof so that the set screw 17 is inserted into the reception cavity 11a of the head 11. The length of the set screw 17 should be short enough not to protrude from the upper surface of the reception cavity 11a of the head 11.

The reception cavity 11a of the head 11 also has an inner thread 11b to be joined to the outer thread 17a of the set screw 17.

The head 11 of the pedicle screw 1 has a rod fixing recess 14 for tightening an end of the rod 2. The rod 2 is inserted into the reception cavity 11a and is put into the rod groove 12 as the end of the rod is tightly inserted into the rod fixing recess 14.

The rod fixing recess 14 and the rod 2 have the same diameter or the diameter of the rod fixing recess 14 is slightly larger than that of the rod 2.

A head cap 18 can be adopted on the upper portion of the head 11 to eliminate the change from a misaligned fixation of the set screw 17. Since the head cap 18 provides an additional support to improve the rod holding power, this can be used as an additional rod such as a fastening element. The head cap 18 is additionally set as needed, not essential.

Figure 9:
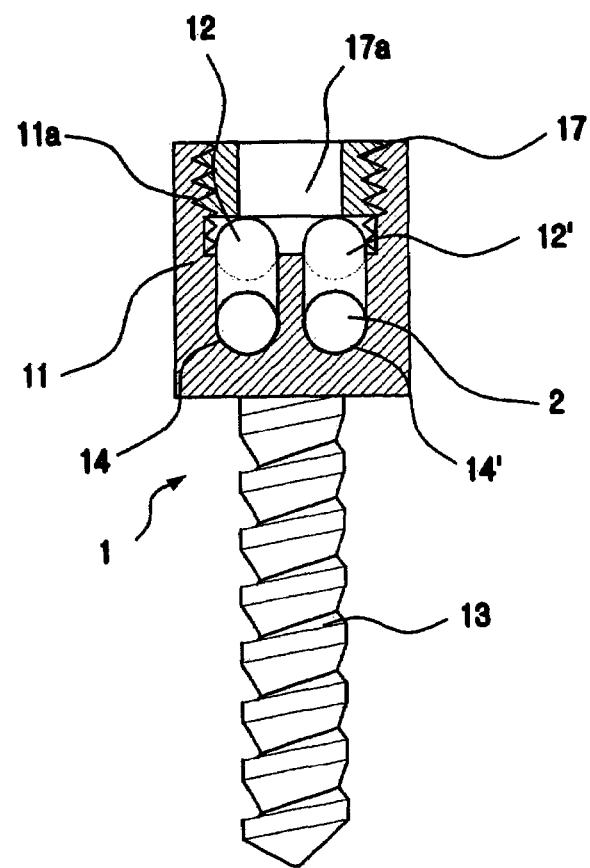
FIG. 9 is a sectional view illustrating a pedicle screw in the first embodiment of the present invention.
Figure 10:
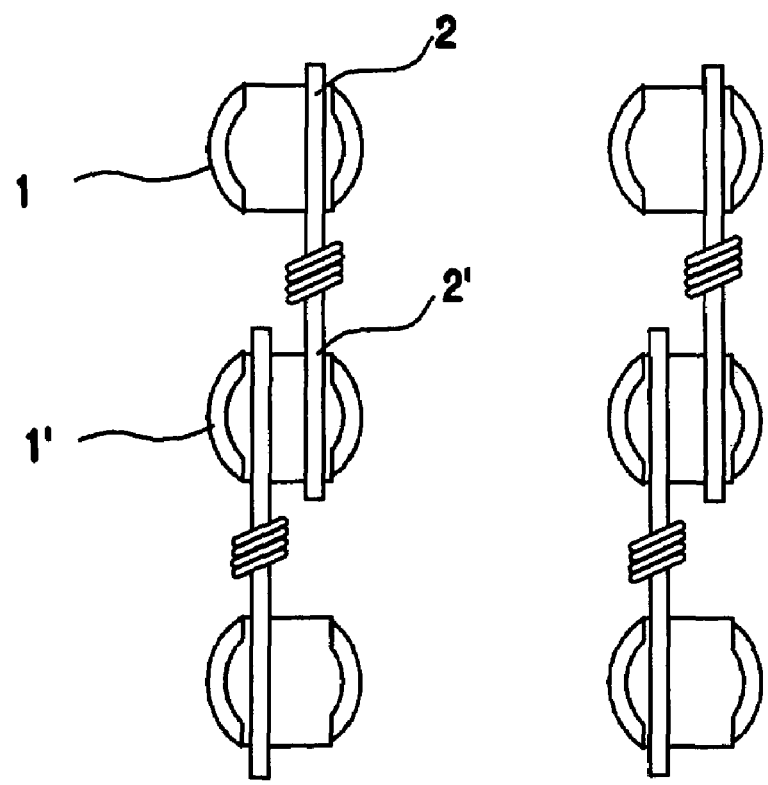
FIG. 10 is a plan view illustrating a serial connection of the rods and the pedicle screws shown in FIG. 9.

The head 11 of the pedicle screw 1 is able to have two rod grooves 12 and 12' and two rod fixing recess 14, 14', as shown in FIG. 9. According to this structure, it is able to serially set the rods 2 without using an additional connector by inserting the rods 2 and 2' into the rod grooves 12 and 12' alternately, as shown in FIG. 10.

The first embodiment of the present invention is restricted within the above structure. For example, the rod can be formed in a straight bar shape or a right angle bar shape which is perpendicular to both ends of the rod body. In such a modified rod, the structure of the pedicle screw 1 is formed with a single rod groove without the rod fixing recess 14. Besides, it may be employed in different structures of the pedicle screw corresponding to the modified rod. Furthermore, the modified rod 2 is securely fixed by the set screw 17 within the reception cavity 11a of the head 11.

A transverse link 3 will be described in detail referring to FIGS. 11 and 12.

The transverse link 3 includes one straight member 31 and two hooks 32 which are respectively extended and bent from both ends of the straight member 31. The transverse link 3 is formed in a rectangular plate. The length of the transverse link 3 is approximately in a range of 20 to 80 mm and it can be adjusted on a basis of unit length of 2 mm. As shown in FIG. 12, the transverse link 3 keeps a space between the rods 2 and 2' by grasping the rods 2 and 2' through the hooks 32. Here, the transverse link 3 of a plate shape has strength to maintain the space between the rods 2 and 2' even if an external force is applied to the rods 2 and 2' and the rods 2 and 2' are then wrenched.

Figure 11:
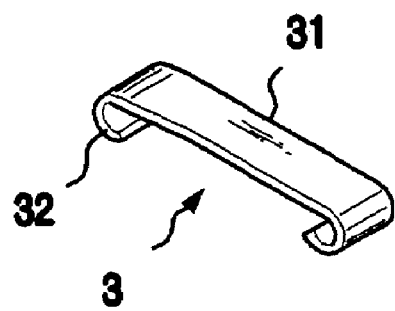
FIG. 11 is a perspective view illustrating a transverse link applied to the rods according to a first embodiment of the present invention.
Figure 12:
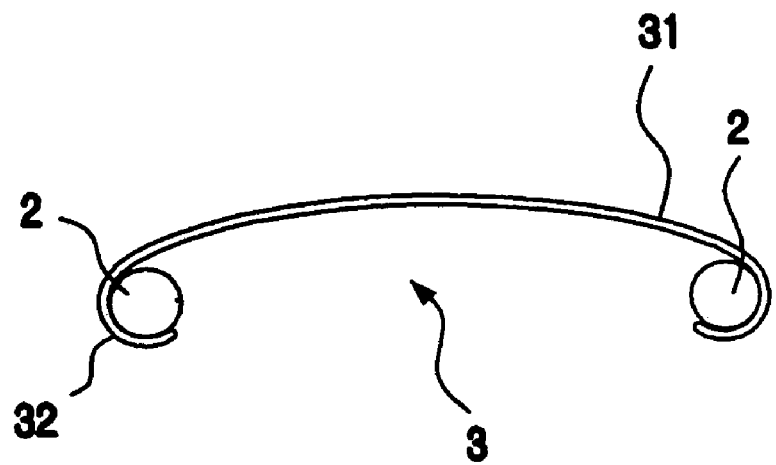
FIG. 12 is a front view illustrating a connection between the transverse link and rods.
Figure 13A:
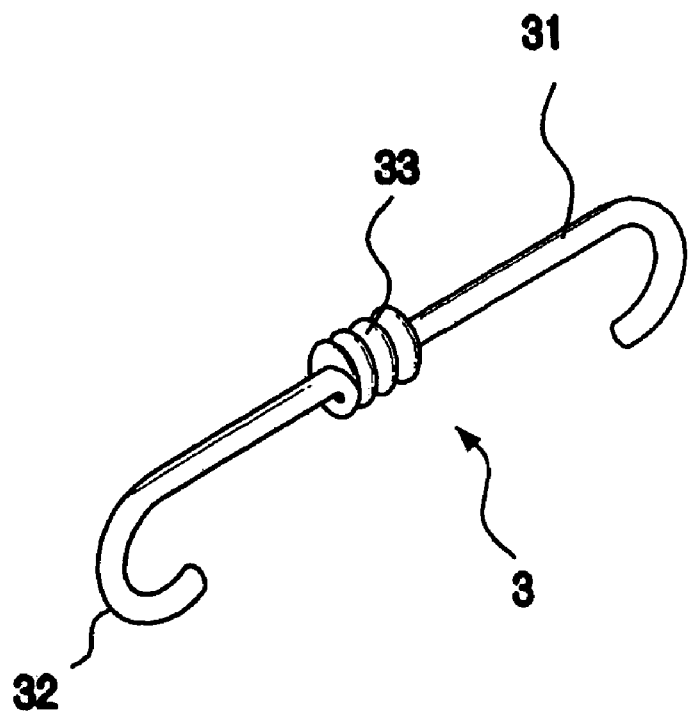
FIG. 13a is a perspective view illustrating another form of the rod.
Figure 13B:
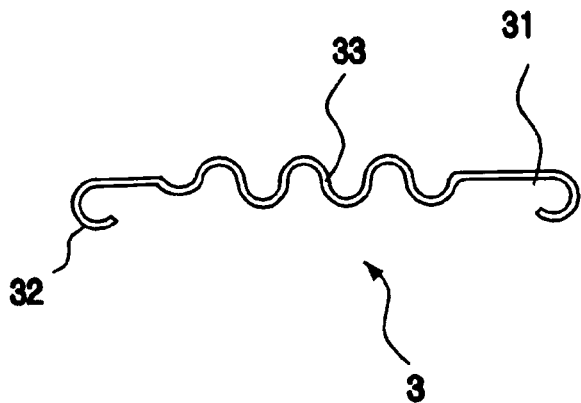
FIG. 13b is a plan view illustrating another form of the rod.

FIG. 13a and FIG. 13b are views illustrating transverse links which are different from that of FIG. 11. That is, an elasticity section 33 is formed in the middle of a straight member 31. The elasticity section 33 has a coil spring as shown in FIG. 13a or a wave shape as shown in FIG. 13b. The elasticity section 33 of the transverse link 3 absorbs a load which is applied to the rod 2.

Figure 14:
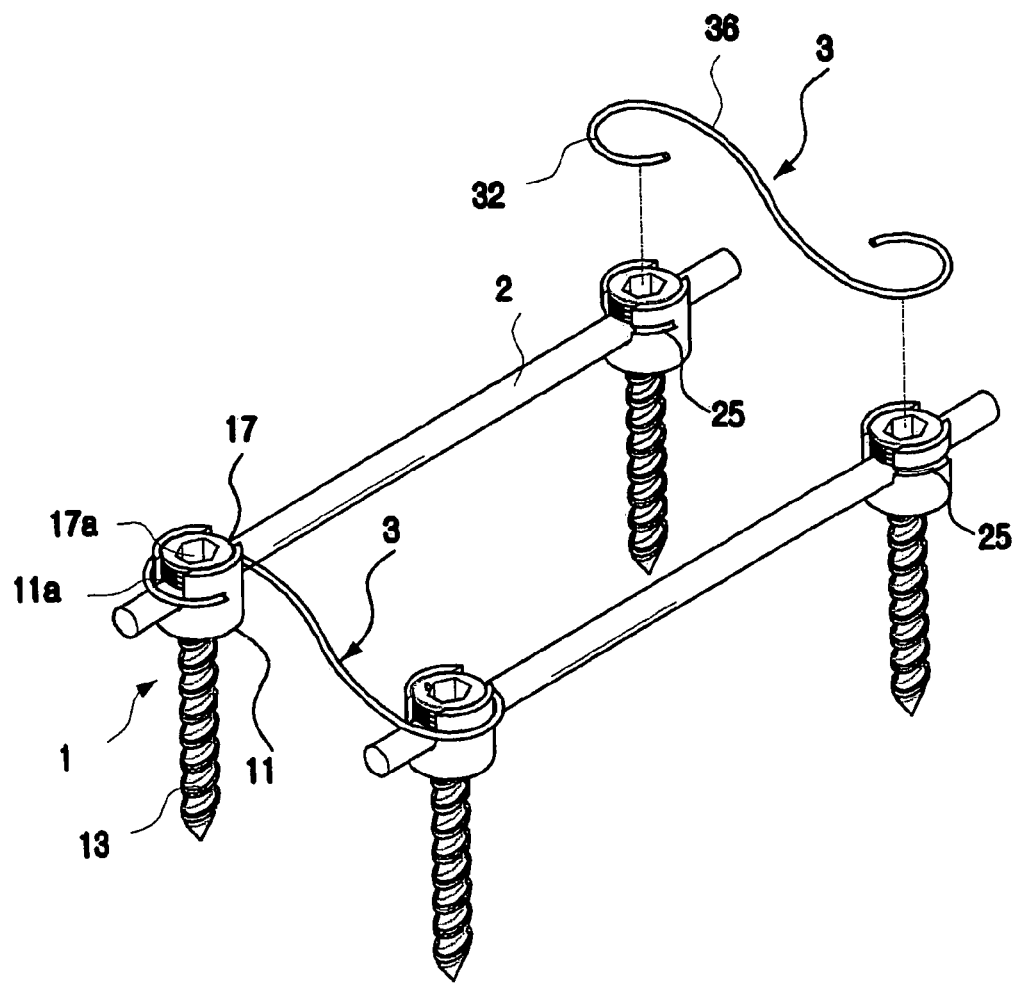
FIG. 14 is a perspective view illustrating a connection between the transverse links to a head of the pedicle screw.

FIG. 14 illustrates an S-shaped transverse link 3 which is different from that of FIG. 11.

The S-shaped transverse link 3 includes one bending member 36 and two hooks 32 which are horizontally extended and bent from both ends of the bending member 36 for holding the head 11 of the pedicle screw 1. A slit 25 is provided on the circumference of the head 11 of the pedicle screw 1 in order to insert the hooks 32 of the S-shaped transverse link 3 into the head 11.

The above-mentioned rods 2 and 2' and transverse links 3 in the first embodiment of present invention are made from a shape memory alloy causing deformation at a specific temperature.

The rods 2 and 2' and the transverse links 3 have a temperature characteristic that they are in a martensite phase at a temperature of +10° C. and below and in an austenite phase at a temperature of more than +35° C. to return back to a memorized original shape. In particular, the deformed shape is kept unchanged up to +26° C. and the memorized shape is gradually restored by a heat treatment up to +35° C.

The rods 2 and 2' and the transverse link 3 are obtained by performing a heat treatment at a temperature of 650° C. to 750° C. for one hour or so, after forming the hooks and elastic section at both ends and the middle section of the shape memory material, respectively. Thus, the rods 2 and 2' and the transverse link 3 have a deforming characteristic at a specific temperature.

Hereinafter, the installation procedures of according to the first embodiment of the present invention will be described in detail.

The pedicle screws 1 are implanted into a selected pedicle of the vertebras in a predetermined angle and depth. At this time, that is not considered configuration of screws that are not well aligned in general. It lengthens the elastic section 16 of the rod 2 by deforming the rod 2 at a temperature of +10° C. and below so that the rod 2 is easily set into the reception cavity 11*a* of the head 11 of the pedicle screw 1, before the rod 2 is inserted into the reception cavity 11*a* of head 11 for coupling the rod 2 to the plurality of the screws 1. Then, the end of the rod 2 of the hook shape is inserted into the rod fixing recess 14, while a deformed straight member (the rod body 15) of the rod 2 is inserted to the rod groove 12 which is formed in the bottom of the reception cavity 11*a* of head 11. The outer thread 17*a* of the set screw 17 is downwardly joined to the reception cavity 11*a* of the head 11 so that the set screw 17 is tightly fixed to the inner thread 11*b* of the reception cavity 11*a* using a wrench tool. The rod 2 is pressed by the set screw 17 and the rod 2 is securely and rigidly fixed to the pedicle screw 1.

After the installation of the rods 2, a heat treatment is applied to the rod 2 at a temperature of more than +35° C. using a surgical heating source. And thus, the lengthened elastic section 16 of the rod 2 is shrunk and returns back to the memorized original shape in the transforming austenite phase. At this time, the end of the hook-shaped rod is rigidly fix to the rod fixing recess 14 of the head 11 while the rode 2 is returning back to the memorized original shape. Thus, both ends of the rod 2 are fixed to the rod fixing recess 14 of the head 11 without any separation.

According to the above mentioned description, although the pedicle screws are not well aligned with others, the rode can be easily and simply connected to the pedicle screw 1 because the rod 2 can be freely bent toward the pedicle screw 1. In additional, the rod 2 provides a movement of between the spinal segments through the superelastic action of the elastic section 16 when the patients bend or wrench his back, after the spine fusion.

In the installing procedures of the rods 2, when the rods 2 and 2' are respectively coupled to the rod grooves 12, the pedicle screw 1 having the two rod grooves 12 and 12 are used. That is, the rods 2 and 2' are respectively and alternately set to the rod grooves 12 and 12' positioned in the reception cavity 11*a*, as shown in FIG. 10. Therefore, in case that the pedicle screw 1 having two rod grooves 12 and 12' are used, it is not necessary to take an additional connector for a serial connection.

Next, an installation procedure of the transverse link 3 will be described in detail.

After coupling the rods 2 and 2' to the pedicle screws 1, the transverse link 3 is hung on a pair of the rods 2 to provide a space between the two rods 2. The installing work of the transverse link 3 is taken in the same manner as it done in the above-mentioned rod installation procedure. That is, it lengthens a body 31 or widens a space of the hooks 32 thereof, by deforming the transverse link 3 at a temperature of +10° C. and below. The deformed hook 32 of the transverse link 3 is inserted into the outer surface of the rod 2. In case of the S-shaped transverse link, it is inserted into a slit 25 of the head 11. After the installation of the transverse link 3, it returns back to the memorized original shape, being transformed to the austenite phase through the heat treatment at a temperature of more than +35° C. so that the transverse link 3 is rigidly fixed on the rod and, in case of the S-shaped transverse link 3, it is fixed on the slit 25 of the pedicle screw 1.

Thus, in case of the above-mentioned structure of the transverse link 3, it easily holds the rod 2 even if a space between the rods 2 and 2' is not in parallel.

Figure 15:
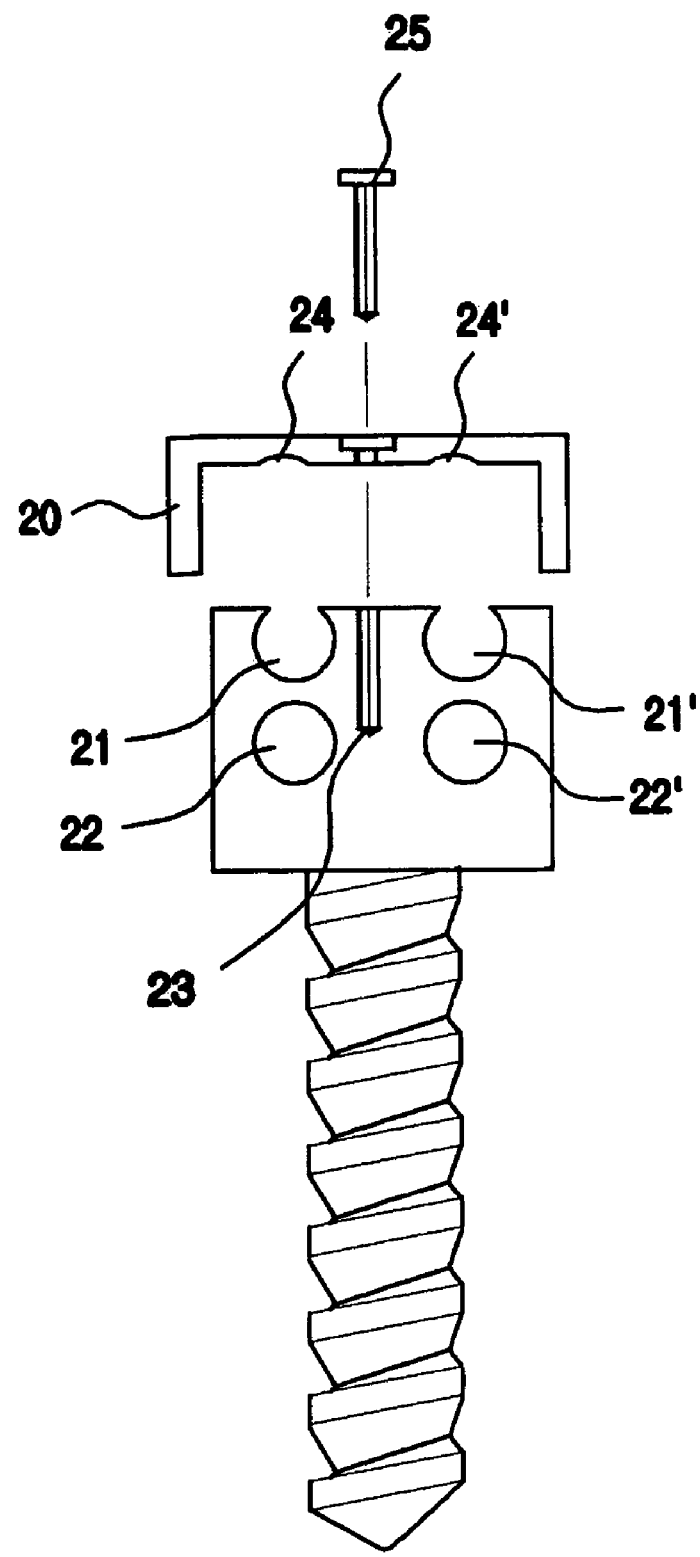
FIG. 15 is a front view illustrating a spine fixation apparatus according to a second embodiment of the present invention.

A second embodiment of the present invention will be described in detail referring to FIG. 15 and the same reference numerals denote the same elements as illustrated in the first embodiment of the present invention.

In the second embodiment, the head 11 of the pedicle screw 1 is formed with a pair of first rod grooves 21 and 21' to locate the rod 2 on an upper portion thereof. Also, a pair of rod inserting recesses 22 and 22' are respectively formed below the rod grooves 21 and 21' and the rod inserting recesses 22 and 22' are positioned in the same axis of the rod grooves 21 and 21', respectively. A female thread 23 is formed on an inner surface of the head 11 at a predetermined depth.

A head cap 20 is provided on the upper portion of the head 11 and the head cap 20 has a pair of second rod grooves 24 and 24' corresponding the first rod grooves 21 and 21'. A fixing screw 25 is joined to the female thread 23 passing through the head cap 20 so that the head 11 is strongly fixed to the head cap 20.

A diameter of the first rod grooves 21 and 21' and the second rod grooves 24 and 24' is correspondent to that of the rods 2 and 2'. And the rod inserting grooves 22, 22' have the same or slightly large diameter than that of the rod 2.

If only one of the first rod grooves 21 and 21' is provided, two female threads may be positioned at both sides of the first rod groove. If two rod grooves are provided, one female thread may be positioned in the middle of the first rod grooves 21 and 21'. In this drawing, the pair of the first rod grooves 21 and 21' are shown. These two grooves are required to serially and alternately set the two rods 2 and 2' on the first rod grooves 21 and 21'.

A third to eight embodiments of the present invention will be described in detail referring to FIGS. 16 to 28.

A rod, a staple rod and a middle connection rod in the these embodiments are made from a shape memory alloy which is in a martensite phase at a temperature of +10° C. and below and in an austenite phase at a temperature of more than +35° C. to return back to the memorized original shape. The shape memory alloy of these embodiments undergoes a preliminary deformation at a temperature of +10° C. and below. A deformed shape is kept unchanged up to temperature +26° C. A shape restoration is occurs under the heating up to +35° C.

Figure 16:
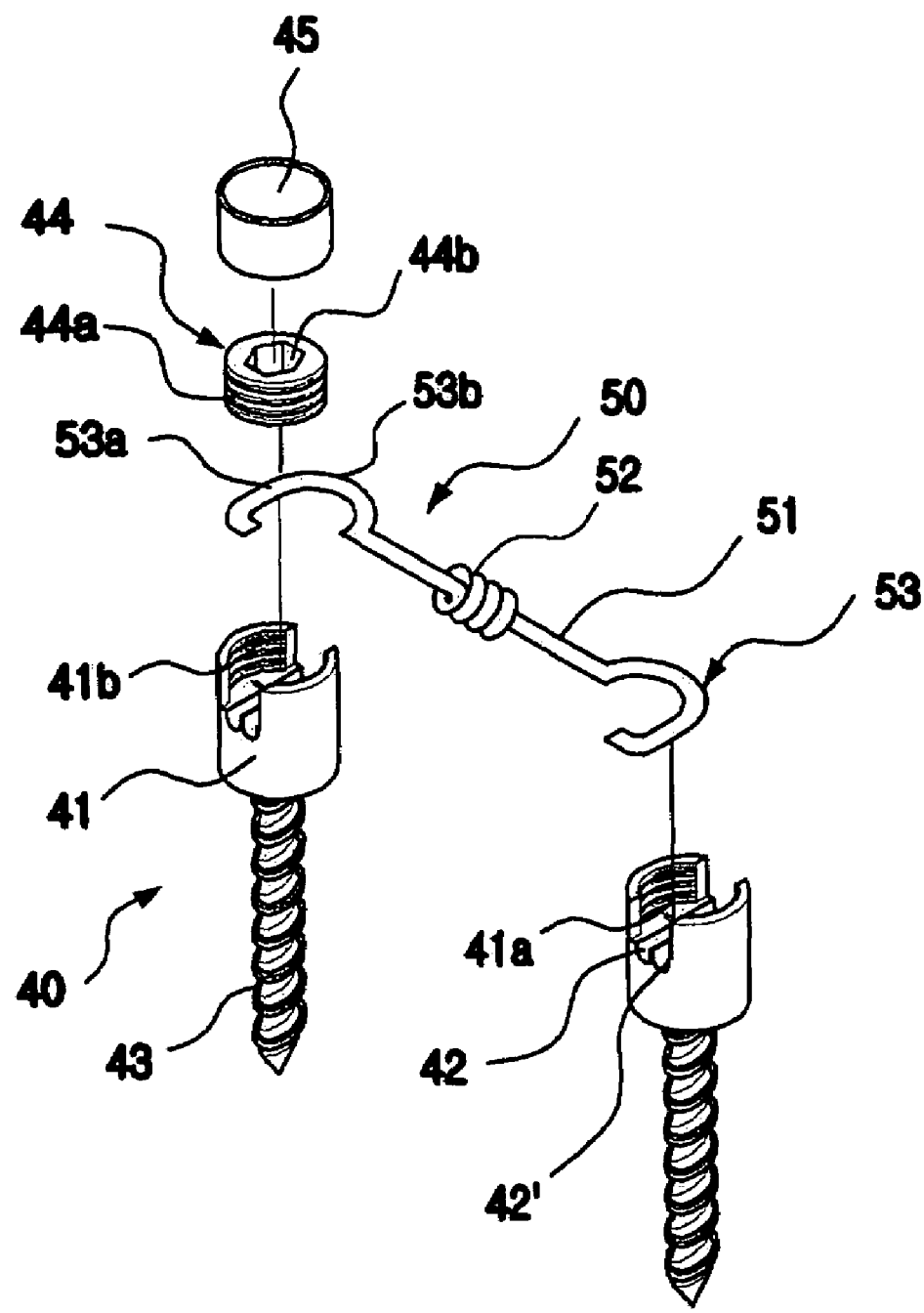
FIG. 16 is a perspective view illustrating a spine fixation apparatus according to a third embodiment of the present invention.

A third embodiment of the present invention will be described in detail referring to FIGS. 16 and 17.

A plurality of pedicle screws 40 according to this embodiment comprises; a head formed at a top portion thereof, wherein the head has a reception cavity 41a and two parallel rod grooves 42 and 42' in bottom surface of the reception cavity 41a; and a thread 43 formed below the head to be implanted into a pedicle of the vertebra.

Two parallel rod grooves 42 and 42' in the reception cavity 41a contributes to a connection of the rods 50 and the pedicle screws 40 without an additional connector. Here, the rod grooves 42, 42' have a diameter equivalent to the rod 50.

A set screw 44 is inserted into the reception cavity 41a of the head 41 of the pedicle screws 40 for preventing a movement of the rod 50. In order to securely tighten the rod 50, the set screw 44 has an outer thread 44a and a recess 44b which has a hexagonal cross-section view in the reception cavity 41a of the head 41. The length of the set screw 44 should be short enough not to protrude from the upper surface of the reception cavity 41a of the head 41. The reception cavity 41a of the head 41 has an inner thread 41b to be joined to the outer thread 44a of the set screw 44.

A head cap 45 can be adopted on the upper portion of the head 41 to eliminate the change from a misaligned fixation of the set screw 44. The head cap 45 serves as an additional supporter to improve the rod holding power using an additional rod-fastening element.

A pair of rods 50 according to this embodiment comprises; a straight bar 51 placed at the center line of the heads; an elastic section 52 formed in the middle of the straight bar 51 to generate an elastic force for absorbing a shock which is inflicted on the patient's vertebra; and a support bar 53 extended from both ends of the straight bar 51 to be put in one of the rod grooves 42 and 42'.

The diameter of the rod is approximately in a range of 2 to 7 mm and it can be adjusted on a basis of unit diameter of 0.5 mm.

The elasticity section 52 is similar to a coil spring. The coil spring is equal to the straight bar 51 in their diameters. The elasticity section 52 can has a wave shape as another form.

The support bar 53 have a line portion 53a, which can be put on one of the rod grooves 42a and 42', and a bending portion 53b which is extend from both ends of the straight bar 51 and curved along the outer surface of the head 41.

The straight bar 51 of the rod 50 is positioned on the central axis of the head 41 by the shape of the support bar 53.

One of the two support bars 53 is opposite to the other in the same head 41; however, the two support bars 53 can be in a reverse phase to each other, even if it is not shown in the drawings. That is, the rod 50 can be serially and alternately connected to the pedicle screw 40 with the support bar 53 of which the bending portions 53b are reversibly positioned and are curved along the outer surface of the heads 41.

Figure 17:
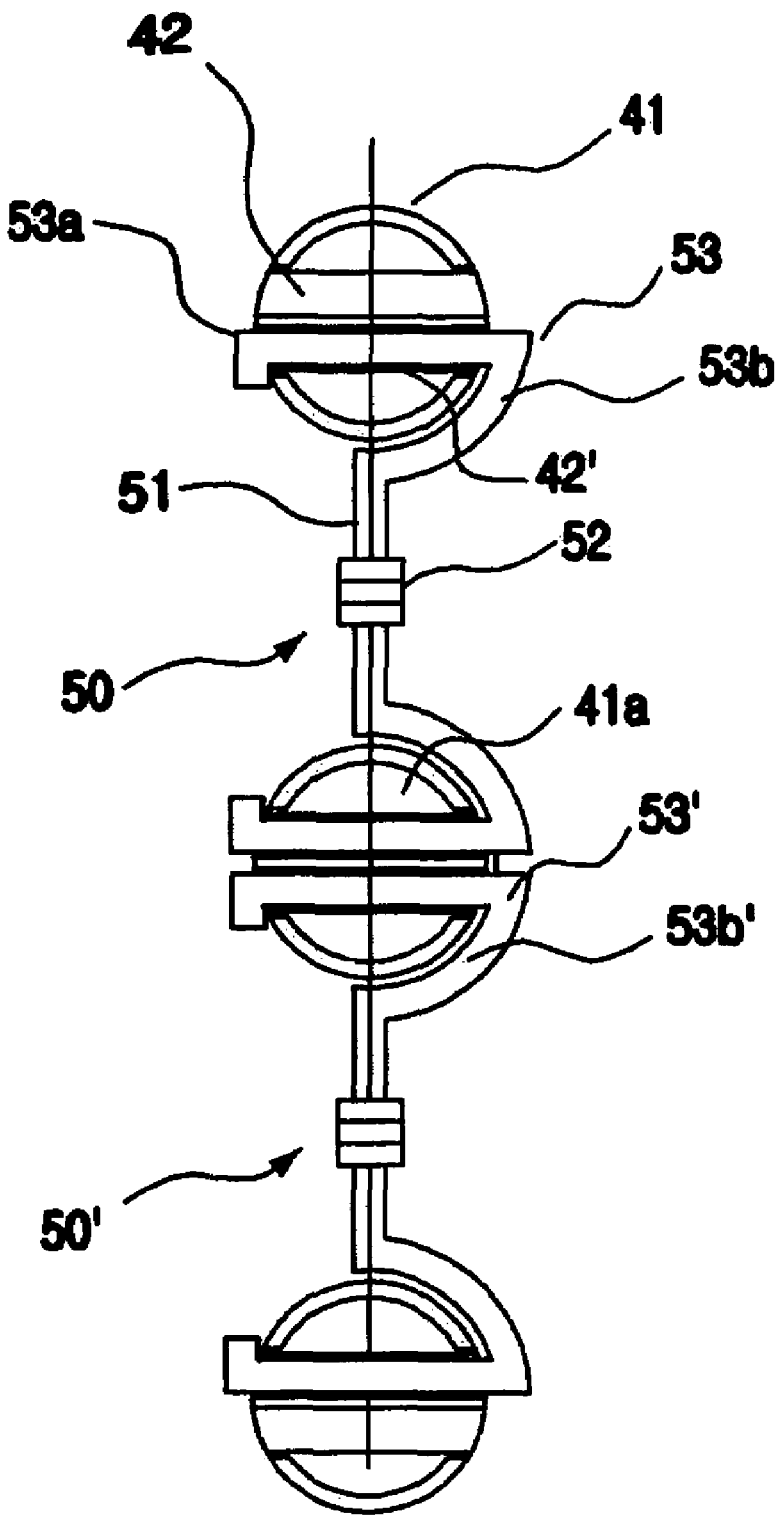
FIG. 17 is a plan view illustrating a serial connection the rods to a head of a pedicle screw shown in FIG. 16.

Referring to FIG. 17, the support bars 53 at both sides of the rod 50 are respectively put into the rod grooves 42 and 42'. Also, the set screws 44 are coupled to the inner threaded 41b of the reception cavity 41a of the head 41, being rigidly fixed to the rod 50.

A forth embodiment of the present invention will be described in detail referring to FIGS. 18 to 20.

Figure 18:
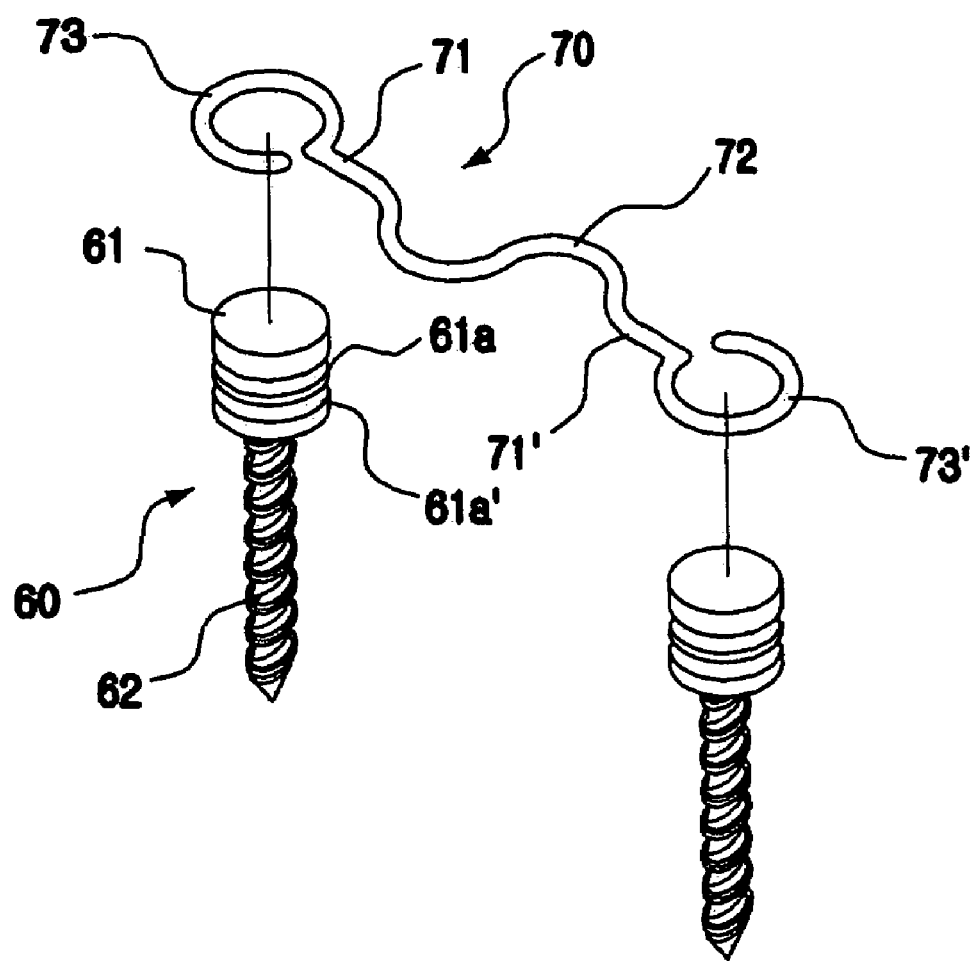
FIG. 18 is a perspective view illustrating a spine fixation apparatus according to a fourth embodiment of the present invention.

Referring now to FIG. 18, it comprises only a plurality of pedicle screws 60 and a rod 70.

The pedicle screws 60 includes a head 61 formed at the top portion thereof and a thread 62 formed below the head 61. The head 61 has first and second circular grooves 61a and 61a' formed in an outer surface thereof.

The rod 70 includes two straight bars 71 and 71' placed at the center line of the head 61 of the pedicle screw 60, an elastic section 72 formed in a type of wave between the two straight bars 71 and 71', and support rings 73 and 73' respectively extended from both ends of the straight bars 71 and 71' to be inserted into one of the first and second circular grooves 61a, 61a'.

The support rings 73 and 73' of the rod 70 are in reverse phase to each other; however, they may be opposite to each other in the same head 61, even if it is not shown in the drawings.

Figure 19:
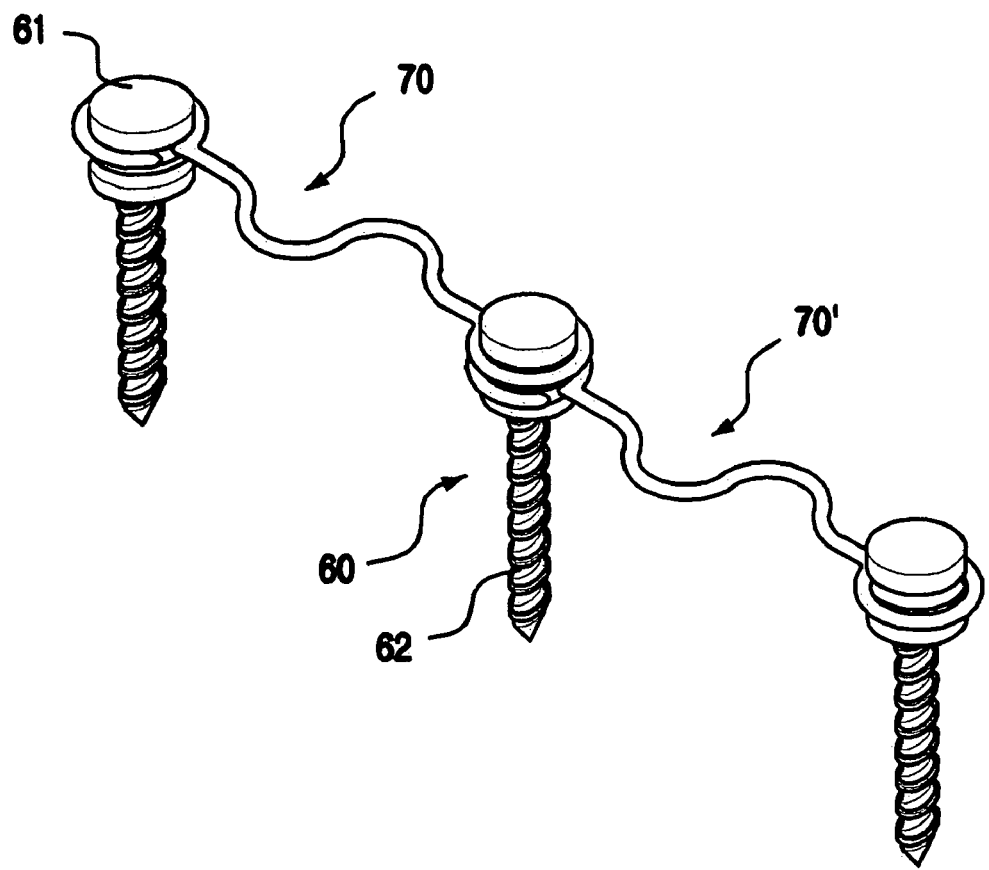
FIG. 19 is a perspective view illustrating a serial connection the rods to a head of a pedicle screw shown in FIG. 18.
Figure 20:
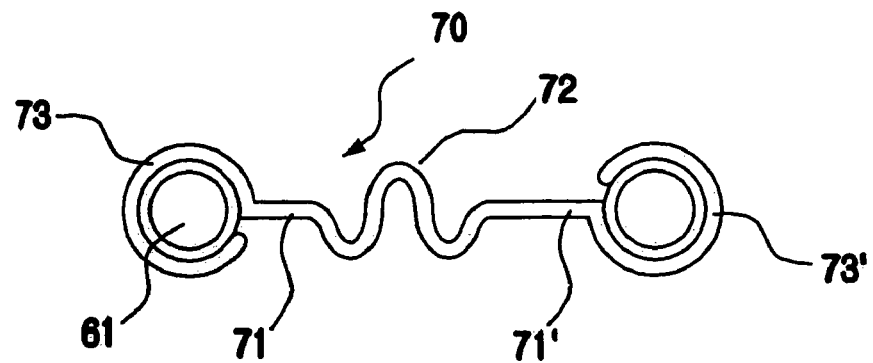
FIG. 20 is a plan view illustrating an assembly of spine fixation apparatus shown in FIG. 18.

Referring now to FIGS. 19 and 20, the rods 70 are serially and alternately connected to the plurality of circular grooves 61a and 61a' of the heads 61 of the pedicle screws 60, using the above support rings 73 and 73'.

A fifth embodiment of the present invention will be described in detail referring to FIG. 21.

Figure 21:
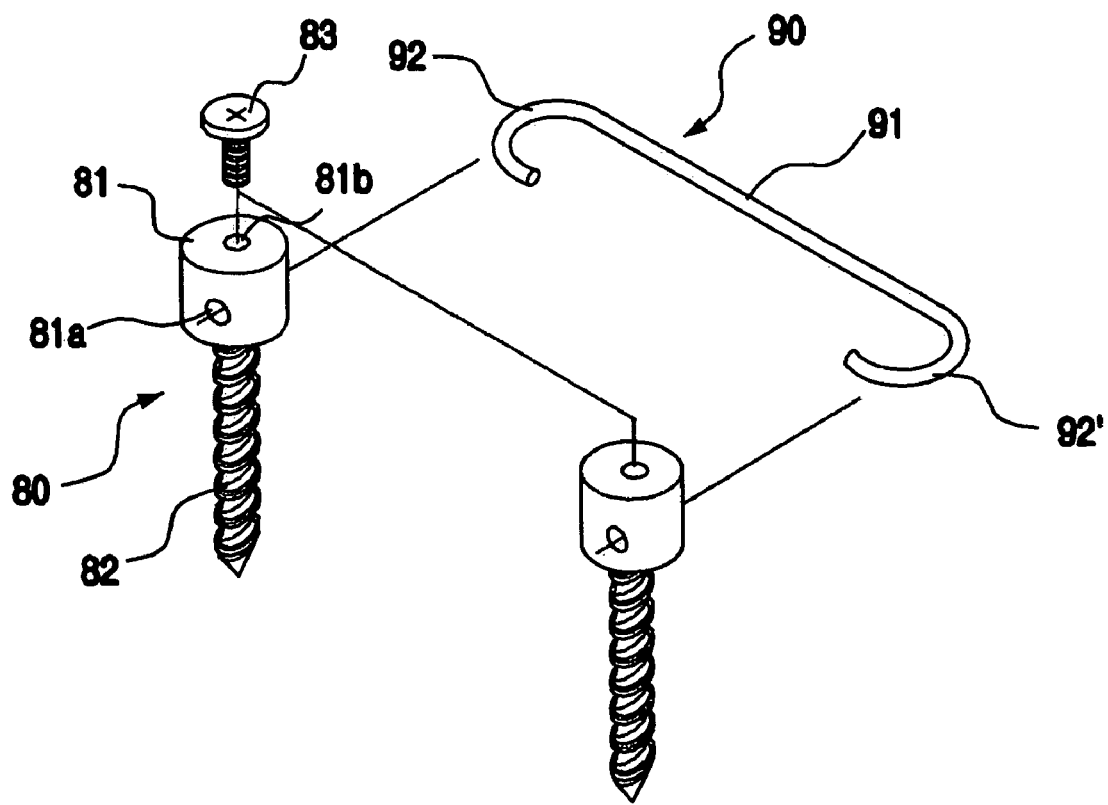
FIG. 21 is a perspective view illustrating a spine fixation apparatus according to a fifth embodiment of the present invention.

Referring now to FIG. 21, the fifth embodiment comprises a plurality of pedicle screws 80 have a head 81, which is formed at the top portion thereof and has a cylindrical type block, and a thread 82 formed below the head 81. The head 81 has an opening 81a horizontally passing through the cylindrical type block to receive both ends of a rod 90 and a thread hole 81b which is upwardly formed and is perpendicular to the opening 81a. The thread hole 81b of the head 81 is joined to a bolt 83 in order to tight the rod 90.

The rod 90 has a straight bar 91 and hooks 92 and 92' which are roundly extended from both ends of the straight bar 91 to be inserted to the opening 81a. The straight bar 91 can be provided with an elastic section in the middle of the rod 90.

Hereinafter, the installation procedure of the rod 90 will be described in detail.

In this embodiment, when the rod 90 is coupled to the pedicle screw 80, the roundly curved hooks 92 of the rod 90 is deformed to a straight bar shape at a temperature +10° C. and below. On the other hand, the straight bar shaped hooks 92 of the rod 90 is inserted to the opening 81a. Thereafter, a heat treatment is applied to the rod 90 at a temperature of more than +35° C. the deformed hooks 92 of the rod 90 are returned back to the memorized original shape and is rigidly fixed to the head 81. After the rod 90 is inserted into the pedicle screw 80, the bolt 83 is joined to the thread hole 81b of the head 81 for tightening the rod 90 to the pedicle screw 80.

A sixth embodiment of the present invention will be described in detail referring to FIG. 22.

This sixth embodiment makes the connecting work simple, by simply coupling the rod to the pedicle screw after a plurality of the pedicle screws are installed in the pedicles of the vertebras.

Figure 22A:
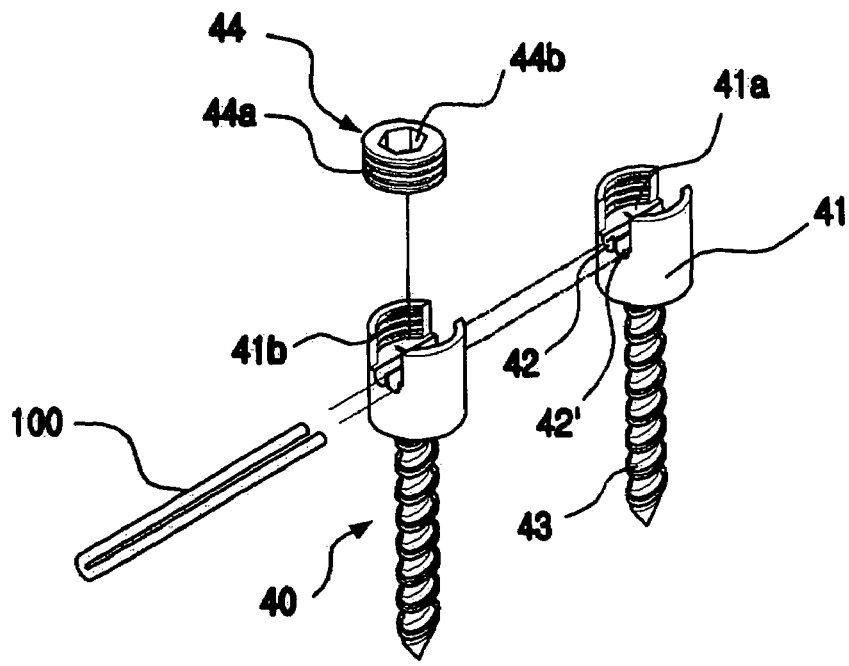
FIGS. 22a and 22b are perspective views illustrating a spine fixation apparatus according to a sixth embodiment of the present invention.

Referring now to FIG. 22a, the detailed description of the pedicle screw will be omitted because the structure of the pedicle screw 40 is the same as that in the above-mentioned third embodiment. The same reference numerals denote the same elements as illustrated in the third embodiment.

A rod 100 of this sixth embodiment is formed in "U" shape. The U-shaped rod 100 is put into the rod grooves 42 and 42' of the head 41, after the pedicle screws 40 is inserted into pedicle of the vertebras. The connecting work of the rod 100 is achieved by tightening the set screw 44 to the reception cavity 41a of the head 41 in order to fix the rod 100 to the pedicle screw 40. If the pedicle screws 40 are not well aligned, the U-shaped rod 100 may be deformed to comply with the misaligned pedicle screw 40. Accordingly, the deformed rod 100 is easily positioned in the rod grooves 42 and 42' of the reception cavity 41a of the head 41. The deformed rod 100 is returned back to the original shape according to a memorized shape of the rod 100, thereby correcting a position of the misaligned pedicle screw 40.

Figure 22B:
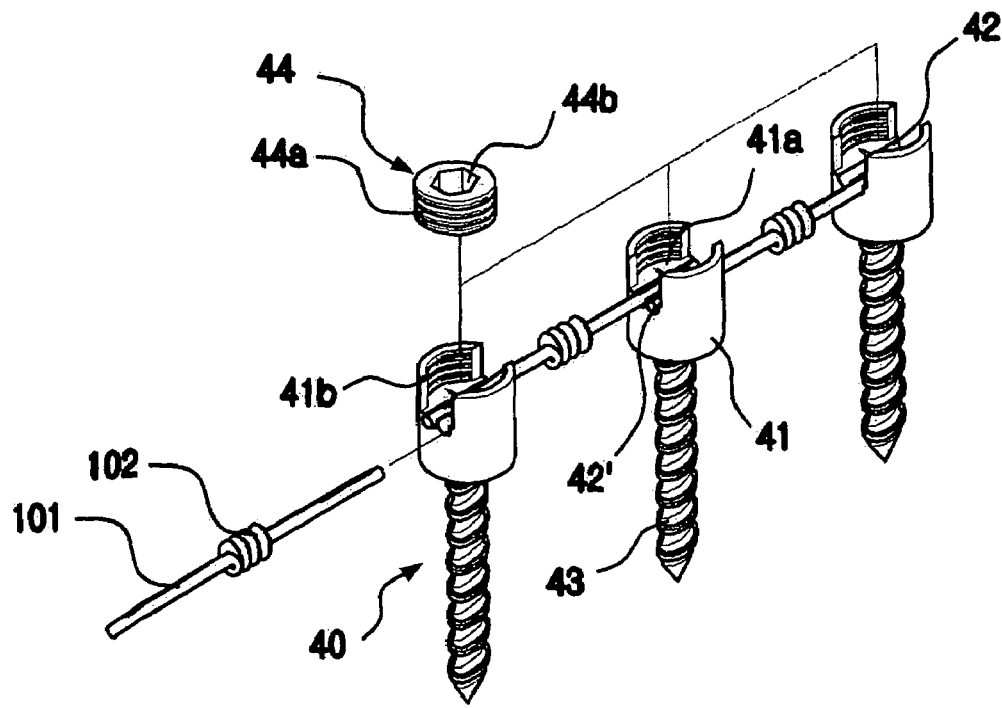

The U-shaped rods 100 can be replaced with a straight bar type rods 101 and 101' as shown in FIG. 22b. An elastic section 102 is provided in the middle of the straight rods 101 and 101'. The straight rods 101 and 101' are respectively and alternately set to the rod grooves 42 and 42' which are positioned in the reception cavity 41a. Therefore, in case that the straight rods 101 and 101' having the elastic section 102 are used, it is not necessary to have an additional connector for such a serial connection.

A seventh embodiment of the present invention will be described in detail referring to FIGS. 23 to 26.

Figure 23:
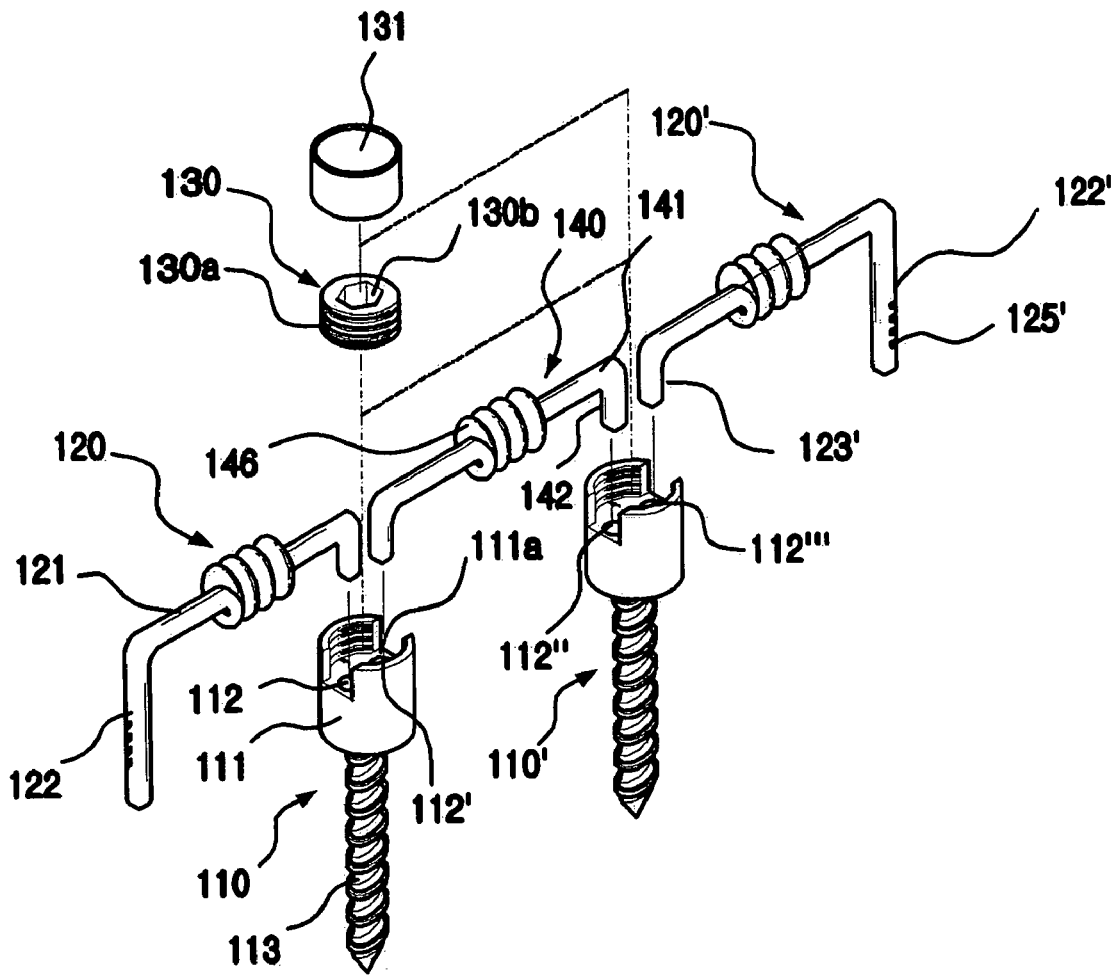
FIG. 23 is a perspective view illustrating a spine fixation apparatus according to a seventh embodiment of the present invention.
Figure 24:
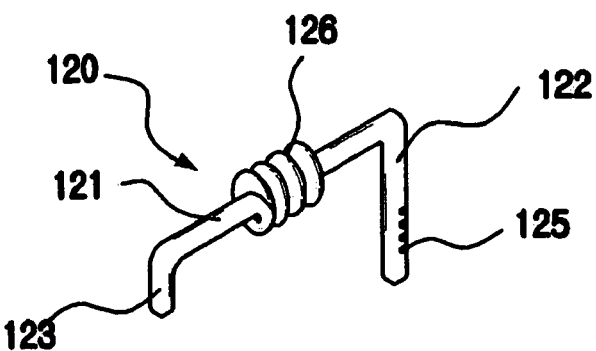
FIG. 24 is a perspective view illustrating a staple rod in the seventh embodiment of the present invention.
Figure 25:
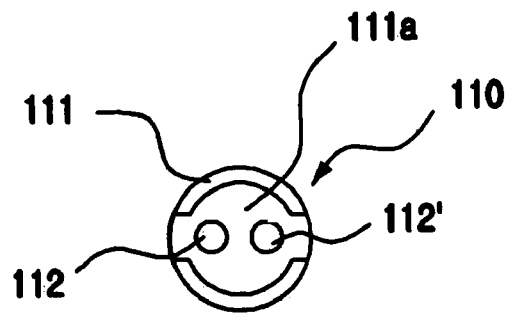
FIG. 25 is plan view illustrating a pedicle screw in the seventh embodiment of the present invention.

Referring now to FIGS. 23 to 25, the seventh embodiment comprises at least one pedicle screw 110, a pair of stapling rods 120, and a middle connecting rod 140.

Referring now to FIG. 25, the pedicle screw 110 has a head 111 at the top portion thereof and a thread 113 formed below the head 111 to be implanted into the pedicle of the vertebra, wherein the head 111 has a reception cavity111a and first and second sockets 112 and 112' formed in the bottom surface of a reception cavity 111a.

The rod 120 is formed in a staple structure for preventing a movement of the vertebra.

One side of the staple rod 120 is directly implanted into the pedicle of the vertebra and other side thereof is inserted into one of the sockets 112 and 112'.

The middle connecting rod 140 is employed for serially connecting the staple rod 120 to the pedicle screw 110 by inserting both ends thereof to the sockets 112 and 112' of the head 111, respectively.

Referring to FIG. 24, the staple rod 120 has a first bridge 121 for providing a space between selected vertebra and adjacent vertebra, an elastic section 126 formed in the middle of the first bridge 121, a spike 122 downwardly extended from one end of the first bridge 121 to be implanted directly into the pedicle of the vertebra, and a first connecting pole 123 downwardly extended from the other end of the first bridge 121 to be fixed to the pedicle screws 110. The length of the first connecting pole 123 is shorter than the depth of the reception cavity 111a of the head 111 so that the first connecting pole 123 is inserted into the socket 112 of the pedicle screw 110. The spike 122 has a plurality of scarred regions 125 for preventing the spike 122 from being detached from the pedicle of the vertebra. The scarred regions 125 may be formed by an electro discharge machine. The diameter of the staple rod 120 is approximately in a range of 2 to 7 mm and it can be adjusted on a basis of unit diameter of 0.5 mm.

Once a spinal fusion has been finished, the staple rod 120 is not separated from the vertebra because the scarred regions 125 are buried in the vertebra.

According to the embodiment of the present invention, it is able to make a connection among three adjacent vertebras, using two staple rods 120 and one pedicle screw 110.

The middle connecting rod 140 has a second bridge 141 for providing a space between the pedicle screws 110, an elastic section 146 formed in the middle of the second bridge 141, and second connecting poles 142 downwardly extended from both ends of the second bridge 141, wherein the length of the second connecting poles 142 is shorter than the depth of the reception cavity111a of the head 111. The reason why is that a volume should be prepared for the insertion of a fixing member such as a set screw.

The first connecting pole 123 of the staple rod 120 and the second connecting poles 142 are substantially equal to each other. In the serial connection, one of the second connecting poles 142 extended at both ends of the middle connecting rod 140 is inserted into the socket 112 of head 111 of the pedicle screw 110 and the other is inserted into the socket 112' of head 111' of the adjacent pedicle screw 110'.

The elastic sections 126 and 146 can be made up of a coil spring or a wave shape element. The diameter of each elastic sections 126 and 146 is substantially the same as that of first and second bridge 121 and 141.

In this embodiment, at least one set screw 130 is joined to the reception cavity 111a of the head 111 of the pedicle screws 110 for preventing a movement of the staple rod 120.

Likewise, in this embodiment, at least one head cap 131 is adopted to the upper surface of the head 111. The head cap 131 is provided to improve holding power of the staple rod 120 without an additional rod such as a fastening element.

Hereinafter, an installation procedure of the staple rod 120 among the first to fourth vertebras will described in detail.

Figure 26:
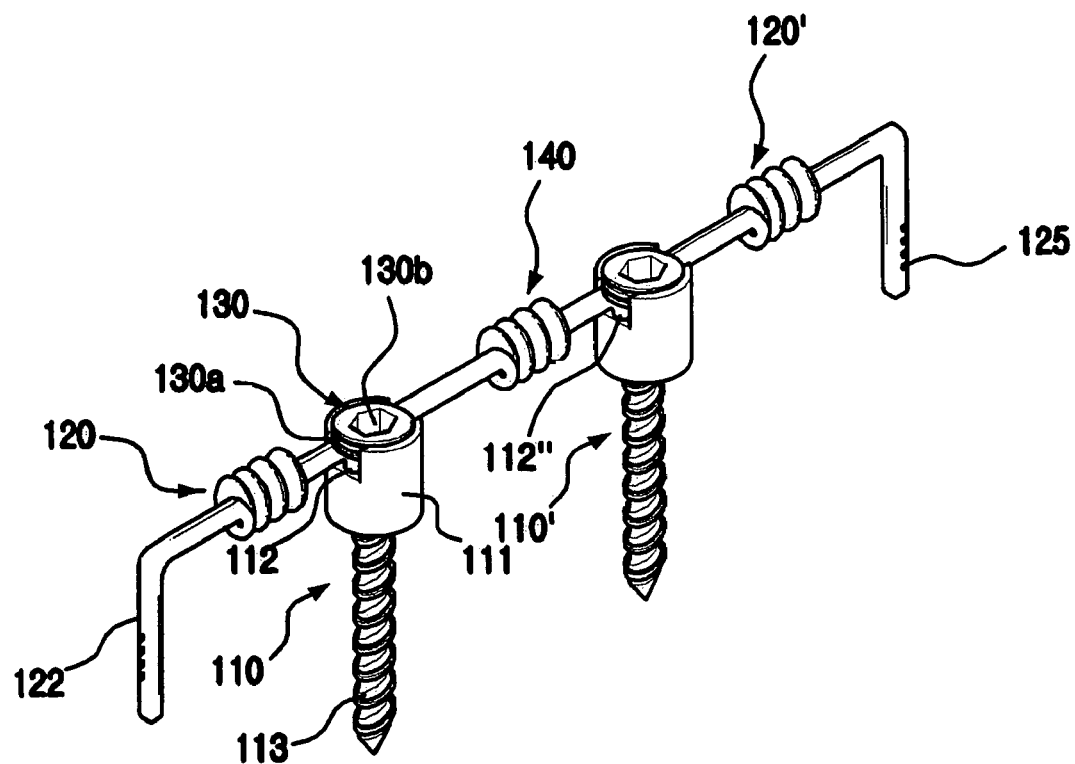
FIG. 26 is a perspective view illustrating a serial connection of the stapling rods to a head of the pedicle screw shown in FIG. 23.

Referring to FIGS. 23 and 26, the first and second pedicle screws 110 and 110' are implanted into second and third middle vertebras, respectively. The first connecting pole 123 of the first staple rod 120 is inserted into one of the sockets 112 and 112' of the first pedicle screw 110 and another connecting bar (123') of the second staple rod 120' is inserted into the socket 112" of the second pedicle screw 110'.

The spikes 122 and 122' of the first and second staple rods 120 and 120' are implanted into the first vertebra and forth vertebra, respectively. The two second connecting poles 142 at both sides of the middle connecting rod 140 are inserted into the sockets 112' an 122" of the first and second pedicle screws 110 and 110, respectively.

After the installation of the staple rods 120 and 120' and the middle connecting rod 140, the outer thread 130a of the set screw 130 is joined to the reception cavity 110a of the head 110 and the set screw 130 is then joined to the inner thread 110b of the reception cavity 110a by a wrench tool. Accordingly, the staple rod 120 and the middle connecting rod 140 are simultaneously pressed by the set screw 130 so that the staple rod 120 and the middle connecting rod 140 are securely and rigidly fixed in the pedicle screw 110. Although the pedicle screws 110 and 110' are not well aligned, the staple rods 120 are easily and simply connected to the pedicle screw 110. This can be further achieved by the deformation of the staple rods 120 and the middle connecting rod 140.

Before the first connecting poles 123 and 123' of the first and second staple rods 120, 120' are inserted into the sockets 112, 112' of the head 111, the staple rod 120 will be deformed at a phase transformation point (+10° C. and below) on condition that one end of the first staple rod 120 is optimally connected to the socket 112 of the head 111. Further, the spikes 122 and 122' of the deformed first and second staple rods 120 and 120' are implanted into bores of the vertebras. Also, the first connecting poles 123 and 123' of the first and second deformed staple rods 120 and 120' are joined to the sockets 112 and 112' of the head 111. Finally, the rod connection is completed among the pedicle screws 110 and 110', the staple rods 120 and 120' and the middle connecting rod 140.

Next, a heat treatment is applied to the staple rods 120 and the middle connecting rod 140 at a restoration point (+35° C. and over), using a surgical tool to have a heating source. The lengthened elastic sections 126 and 146 are returned back to the memorized original shape and are transformed to an austenite phase.

At this time, the first and second connecting poles 123 and 142, the staple rod 120 and the middle connecting rod 140 is rigidly fixed to the sockets 112 and 112' of the head 110, during the restoration to the memorized original shape.

According to this embodiment, a movement between spinal segments is given by the superelastic action of the elastic section 126 and 146, which are respectively formed in the staple rod 120 and the middle connecting rod 140, when the patients bend or wrench his back after the spine fusion.

According to the above-mentioned structure of the seventh embodiment, the first and second staple rods 120 and 120' are formed in the symmetric structure. Thus, it is necessary to have four pedicle screws even though all of them are needed in the conventional spinal fixation system; however, it is necessary to have only two pedicle screws in the present invention. Therefore, according to this embodiment, the number of the pedicle screw is reduced. In particular, in case of the correction of two vertebras, it may be possible to perform the correcting work of the vertebras by using only one single staple rod 120 without an additional pedicle screw. In case of correction of three vertebras, it is necessary to have only one pedicle screw.

An eighth embodiment of the present invention will be described in detail referring to FIGS. 27 and 28.

In this embodiment, the staple rod 150 is directly implanted into the pedicle of the vertebra without any pedicle screw.

Figure 27:
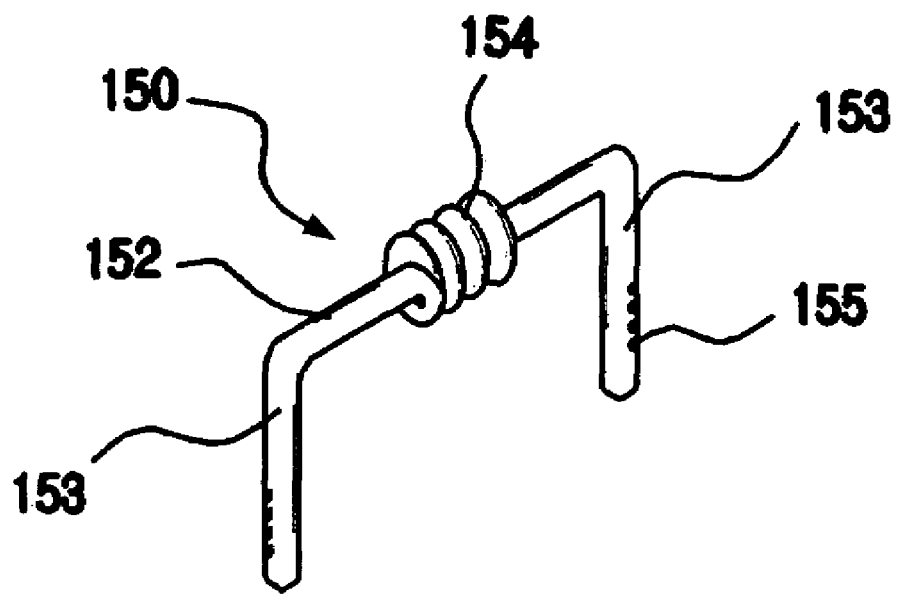
FIG. 27 is a perspective view illustrating a spine fixation apparatus according to an eight embodiment of the present invention.
Figure 28:
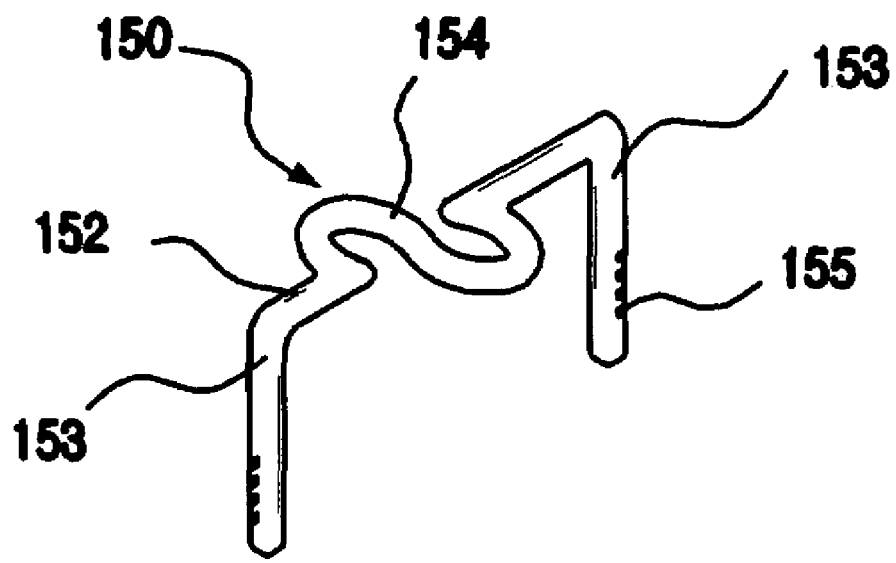
FIG. 28 is a perspective view illustrating another form of the staple rod.

Referring now to FIGS. 27 and 28, at least one staple rod 150 is located at both laterals of the spine.

The staple rod 150 has a bridge 152 for providing a space between a selected vertebra and an adjacent vertebra, a spike 153 downwardly extended from both ends of the bridge 152 for implantation into the pedicle of the vertebra, and an elastic section 154 formed in the bridge 152.

The elastic section 154 can be made of a coil spring (see FIG. 27) or a wave shape element or a S-shaped element (see FIG. 28). Also, The spike 153 has a plurality of scarred regions 155 which prevents the spike 153 from being detached from the pedicle of the vertebra.

The scarred regions 125 may be formed by an electro discharge machine.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

According to the first to eighth embodiment of the present invention, the rods and transverse links are made of a shape memorized Nitinol alloy (Ni—Ti alloy) which has a super-elastic characteristic. Thus, although the pedicle screws are out of alignment during the surgery, the present invention can easily and simply make a structural connection between the rods and the pedicle screws without excessive force on the spine and/or implants.

In addition, in the present invention, the rods and transverse links have an elastic section in an optional range thereof. The elasticity section of the rod allows a delicate movement after the spinal segments fusion. Thus, it disperses a load, which is put on the spinal segments which have been fused, through the rods and the transverse links having super-elasticity. As a result, a burden on lumbar vertebra is reduced. Also, in case of using the spinal fixation apparatus of the present invention, it has another effect on the decrease of a complication that can be caused between an upper segment and a lower segment.

What is claimed is:

1. A spinal fixation apparatus comprising:
 a plurality of pedicle screws, each of which has a head formed at a top portion thereof and a thread formed below the head to be implanted into a pedicle of a vertebra, wherein the head has a reception cavity and two parallel rod grooves in a bottom surface of the reception cavity;
 a rod connected to a first pedicle screw and a second pedicle screw of said plurality of pedicle screws for preventing a movement of the vertebra, wherein said rod is made of a shape memory alloy which can be transformed at a designated temperature and wherein said each rod includes:
  1) a straight bar placed in line with a center of the heads of said first and second pedicle screws of said plurality of pedicle screws;
  2) an elastic section formed in the straight bar; and
  3) a first support bar disposed at a first end of said rod and a second support bar disposed at a second end of said rod, opposite said first end, said first support bar having a first bending portion extending from a first end of the straight bar and bent along a first outer surface of the head of said first pedicle screw, said second support bar having a second bending portion extending from a second end of the straight bar and bent along a second outer surface of the head of said second pedicle screw, said first support bar further having a first line portion extending from said first bending portion, and said second support bar further having a second line portion extending from said second bending portion, wherein said first support bar is received in a first rod groove of said two parallel rod grooves associated with said head of said first pedicle screw of said plurality of pedicle screws and said second support bar is received in a second rod groove of said two parallel rod grooves associated with said head of said second pedicle screw of said plurality of pedicle screws, and
 a plurality of set members, each of said plurality of set members being inserted into a respective reception cavity of the head of a respective pedicle screw of said plurality of pedicle screws for preventing a movement of said rod.

2. The spinal fixation apparatus according to claim 1, wherein said rod is in a martensite phase at a temperature of approximately +10° C. and below and is in an austenite phase at a temperature of approximately +35° C. and over.

3. The spinal fixation apparatus according to claim 1, wherein said elastic section of said rod has a coil spring shape.

4. The spinal fixation apparatus according to claim 1, further comprising a plurality of head caps, each of said plurality of head caps being joined to the head of a respective pedicle screw of said plurality of pedicle screws.

* * * * *